United States Patent
Greider et al.

(10) Patent No.: US 6,300,131 B1
(45) Date of Patent: Oct. 9, 2001

(54) TELOMERASE-ASSOCIATED PROTEINS

(75) Inventors: Carol W. Greider; Siyuan Le, both of Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/286,959

(22) Filed: Apr. 6, 1999

Related U.S. Application Data

(60) Provisional application No. 60/080,783, filed on Apr. 6, 1998.

(51) Int. Cl.[7] ............................ C07H 21/04; C07K 14/00; C07K 16/00; C12N 15/86; C12N 15/85
(52) U.S. Cl. ..................... 435/375; 435/91.1; 435/69.1; 435/320.1; 435/325; 536/23.1; 536/23.5; 530/350; 530/387.1
(58) Field of Search ........................... 435/6, 91.1, 69.1, 435/320.1, 375, 325, 455; 536/23.1, 23.5, 24.3, 24.31, 24.33, 24.5; 530/350, 387.1; 514/44

(56) References Cited

PUBLICATIONS

Wickham et al., "Mammalian Staufen is a Double–stranded RNA and Tubulin Binding Protein which Localizes to the Rough Endoplasmic Reticulum", Molecular and Cellular Biology, pp. 2220–2230, Mar. 1999.*

Berendsen, "A Glimpse of the Holy Grail?", Science, vol. 282, pp. 642–643, Mar. 1999.*

Branch TIBS 23, 1998, pp. 45–50.*

Crooke "Antisense Research & Applications" pp. 1–50, 1998.*

Adams et al., "3,400 new expressed sequence tags identify diversity of transcripts in human brain", *Nature Genetics*, 4:256–267.

Genbank Accession No. 317397, Adams, MD., May 25, 1993.

Desgroseillers, L., et al., Localization of a Human Double–Stranded RNA–binding protein Gene (STAU) to Band 20q13.1 by Fluorescence in Situ Hybridization Genomics, 1996, Genomics, 36, 3: pp. 527–529.

Ferrandon, D., et al., RNA–RNA Interaction is Required for the Formation of Specific Bicoid–mRNA 3' UTR–STAUFEN Ribonucleo–protein Particles, 1997, The EMBO Journal, 16, 7: PP. 1751–1758.

* cited by examiner

*Primary Examiner*—John S. Brusca
*Assistant Examiner*—Karen A Lacourciere
(74) *Attorney, Agent, or Firm*—Fish & Richardson P.C.

(57) ABSTRACT

A human staufen polypeptide that is associated with telomerase is described. Methods for inhibiting telomerase activity also are described.

24 Claims, 12 Drawing Sheets

```
TEP3-2  LNKSEISQVFETALKRNLPVNFEVARESGEHMKNFVTKVSVGEFVGEGEGKSKKISKKNAAIAVLEELKKLP
STAU-1  KDKTPMCLVNELARYNKITHQYRLTEERGPAHCKTFTVTLMLQDEEYSADGFKIKAQHLAASKAIEETMYKH
STAU-3  DKKSPISQVHEIGIKRNMTVHFKVLREEGPAHMKNFITACIVGSIVTEGEGNQKHVSKKRAAEKMLVELQKLP

TEP3-3  QGINPISRLAQIQQAKKEKEPEYTLLTERQ     LPRRREFVMQVKVGNHTAEGTGTNKKVAKANAAENMLILGFKV
STAU-4  DADNPITKLIQLQQTRKEKEHIFEIIAKNGNETARRREFVMEVSASGSTARGTCNSKKILAKRNAAQALFELLEAV

TEP3-1  GKGKTRQAAKHDAAAKAIIRIL
TEP3-4  GIGKDVESCHDMAAIINILKKLL
STAU-2  GIGRTLQQAKHDAAARAIQVL
STAU-5  GVGKSSEESQNDAAISNALKIL
```

FIG. 1B

SEQUENCE LISTING

<160> NUMBER OF SEQ ID NOS: 24

<210> SEQ ID NO 1
<211> LENGTH: 3190
<212> TYPE: DNA
<213> ORGANISM: Homo sapiens

<400> SEQUENCE: 1

| | | | | | |
|---|---|---|---|---|---|
| ctagaattca | gcggccgctg | aattctaggg | cggctgccgc | gtccctctcg | gctcccgctt | 60 |
| cctttgaccg | cctccccccc | ccggcccggc | ggcgcccgcc | tcctccacgg | ccactccgcc | 120 |
| tcttccctcc | cttcgtccct | tcttcctctc | ccttttttcc | ttcttccttc | ccctcctcgc | 180 |
| cgccaccgcc | caggaccgcc | ggccggggga | cgagctcgga | gcagcagcca | gagtttatta | 240 |
| accacttaac | ctctcagaac | tgaacaaaga | caacattgtt | cctggaacgc | cctctttta | 300 |
| aaaagaaag | cataacccct | actgtagaac | taaatgcact | gtgcatgaaa | cttggaaaaa | 360 |
| aaccaatgta | taagcctgtt | gacccttact | ctcggatgcg | gtccacctat | aactacaaca | 420 |
| tgagaggagg | tgcttatccc | ccgaggtact | tttacccatt | tccagttcca | cctttacttt | 480 |
| atcaagtgga | actttctgtg | ggaggacagc | aatttaatgg | caaggaaag | acaagacagg | 540 |
| ctgcgaaaca | cgatgctgct | gccaaagcgt | tgaggatcct | gcagaatgag | cccctgccag | 600 |
| agaggctgga | ggtgaatgga | agagaatccg | aagaagaaaa | tctcaataaa | tctgaaataa | 660 |
| gtcaagtgtt | tgagattgca | cttaaacgga | acttgcctgt | gaatttcgag | gtggcccggg | 720 |
| agagtggccc | accccacatg | aagaactttg | tgaccaaggt | ttcggttggg | gagtttgtgg | 780 |
| gggaaggtga | agggaaaagc | aagaagattt | caaagaaaaa | tgccgccata | gctgttcttg | 840 |
| aggagctgaa | gaagttaccg | cccctgcctg | cagttgaacg | agtaaagcct | agaatcaaaa | 900 |
| agaaaacaaa | acccatagtc | aagccacaga | caagcccaga | atatggccag | gggatcaatc | 960 |
| cgattagccg | actggcccag | atccagcagg | caaaaaagga | gaaggagcca | gagtacacgc | 1020 |
| tcctcacaga | gcgaggcctc | ccgcgccgca | gggagtttgt | gatgcaggtg | aaggttggaa | 1080 |
| accacactgc | agaaggaacg | ggcaccaaca | agaaggtggc | caagcgcaat | gcagccgaga | 1140 |
| acatgctgga | gatccttggt | ttcaaagtcc | cgcaggcgca | gcccaccaaa | cccgcactca | 1200 |
| agtcagagga | gaagacaccc | ataaagaaac | caggggatgg | aagaaaagta | acctttttg | 1260 |
| aacctggctc | tggggatgaa | aatgggacta | gtaataaaga | ggatgagttc | aggatgcctt | 1320 |
| atctaagtca | tcagcagctg | cctgctggaa | ttcttcccat | ggtgcccgag | gtcgcccagg | 1380 |
| ctgtaggagt | tagtcaagga | catcacacca | aagattttac | cagggcagct | ccgaatcctg | 1440 |
| ccaaggccac | ggtaactgcc | atgatagccc | gagagttgtt | gtatggggc | acctcgccca | 1500 |
| cagccgagac | cattttaaag | aataacatct | cttcaggcca | cgtacccat | ggacctctca | 1560 |
| cgagaccctc | tgagcaactg | gactatcttt | ccagagtcca | gggattccag | gttgaataca | 1620 |
| aagcttccc | caaaacaac | aagaacgaat | ttgtatctct | tatcaattgc | tcctctcagc | 1680 |
| cacctctgat | cagccatggt | atcggcaagg | atgtggagtc | ctgccatgat | atggctgcgc | 1740 |
| tgaacatctt | aaagttgctg | tctgagttgg | accaacaaag | tacagagatg | ccaagaacag | 1800 |
| gaaacggacc | aatgtctgtg | tgtgggaggt | gctgaacctt | ttctggccat | gaaccattat | 1860 |
| aaaatcccaa | catatatact | gaaaatactg | aaactgcttt | gaaaatttgg | aatttctgat | 1920 |
| acctccagtg | ggccgagaga | cacggtgggt | aaaggatgtg | ggcagcagca | gggaagacaa | 1980 |
| cagaaacaca | aggaggcggc | tgtggccggg | ctggactgtg | ctggggtttg | ttgtgatggc | 2040 |

-continued

```
cactcggtga cctggcggtc cctacgcaat agcagctgcc tgtggggaag aagggctgcc    2100
cagccagctg gttctcccgg gacaccagca gatccacacc ctgggcacct ccgtgtttgg    2160
tctttttttt ccctgtgtg aaagaagaaa cggcacgacc ccttctcaag ctggctcact     2220
cagacacatt gggacaaacc ctggacagcc atgccagaga gaggcctttg accggcccca    2280
gagctaaaag caccagagaa atcaaatgc ttcctactca gcgtgaccca acttttctag     2340
tgtgccacgg ccccaccacc tcctgcagta cccacaccat caccactgct ttctcttcca    2400
acagtgatct gtattcttag tttcattatt ttcttttgat tgatatgaca ctatataaaa    2460
ttttcatttg agaatttctc aattgtatct agttaaatag cacagtttgg aaacttgtct    2520
gagactgact ttatcaataa tctaaccgac aaagatcata tccatgtgta tgtggttaga    2580 cattttatt tcattgacta acccaggaca gtttcagtga tgcaaattgt gtgccctctg     2640
gttcagctga acagtcctg gactttcaaa accttgaat aagtctccca cagttgtata     2700
aattggacaa tttaggaatt ttaaacttta gatgatcatt tggttccatt tttatttcat    2760
ttttattttt gttaatgcaa acaggactta atgaactttt gatctctgtt ttaaagatta    2820
ttaaaaaaca ttgtgtatct atacatatgg ctcttgagga cttagctttc actacactac    2880
aggatatgat ctccatgtag tccatataaa cctgcagagt gattttccag agtgctcgat    2940
actgttaatt acatctccat tagggctgaa agaatgacc tacgtttctg tatacagctg     3000
tgttgctttt gatgttgtgt tactgtacac agaagtgtgt gcactgaggc tctgcgtgtg    3060
gtccgtatgg aaagcctggt agccctgcga gttaagtact gcttccattc attgtttacg    3120
ctggaatttt tctccccatg gaatgtaagt aaaacttaag tgtttgtcat caataaatgg    3180
taatacttaa                                                          3190
```

<210> SEQ ID NO 2
<211> LENGTH: 496
<212> TYPE: PRT
<213> ORGANISM: Homo sapiens

<400> SEQUENCE: 2

```
Met Lys Leu Gly Lys Lys Pro Met Tyr Lys Pro Val Asp Pro Tyr Ser
 1               5                  10                  15

Arg Met Arg Ser Thr Tyr Asn Tyr Asn Met Arg Gly Gly Ala Tyr Pro
                20                  25                  30

Pro Arg Tyr Phe Tyr Pro Phe Pro Val Pro Pro Leu Leu Tyr Gln Val
            35                  40                  45

Glu Leu Ser Val Gly Gly Gln Gln Phe Asn Gly Lys Gly Lys Thr Arg
        50                  55                  60

Gln Ala Ala Lys His Asp Ala Ala Lys Ala Leu Arg Ile Leu Gln
65                  70                  75                  80

Asn Glu Pro Leu Pro Glu Arg Leu Glu Val Asn Gly Arg Glu Ser Glu
                85                  90                  95

Glu Glu Asn Leu Asn Lys Ser Gly Ile Ser Gln Val Phe Glu Ile Ala
            100                 105                 110

Leu Lys Arg Asn Leu Pro Val Asn Phe Glu Val Ala Arg Glu Ser Gly
        115                 120                 125

Pro Pro His Met Lys Asn Phe Val Thr Lys Val Ser Val Gly Glu Phe
    130                 135                 140

Val Gly Glu Gly Glu Gly Lys Ser Lys Lys Ile Ser Lys Lys Asn Ala
145                 150                 155                 160
```

```
Ala Ile Ala Val Leu Glu Glu Leu Lys Lys Leu Pro Leu Pro Ala
                165                 170                 175

Val Glu Arg Val Lys Pro Arg Ile Lys Lys Thr Lys Pro Ile Val
                180                 185                 190

Lys Pro Gln Thr Ser Pro Glu Tyr Gly Gln Gly Ile Asn Pro Ile Ser
                195                 200                 205

Arg Leu Ala Gln Ile Gln Gln Ala Lys Lys Glu Lys Glu Pro Glu Tyr
    210                 215                 220

Thr Leu Leu Thr Glu Arg Gly Leu Pro Arg Arg Arg Glu Phe Val Met
225                 230                 235                 240

Gln Val Lys Val Gly Asn His Thr Ala Glu Gly Thr Gly Thr Asn Lys
                245                 250                 255

Lys Val Ala Lys Arg Asn Ala Ala Glu Asn Met Leu Glu Ile Leu Gly
                260                 265                 270

Phe Lys Val Pro Gln Ala Gln Pro Thr Lys Pro Ala Leu Lys Ser Glu
                275                 280                 285

Glu Lys Thr Pro Ile Lys Lys Pro Gly Asp Gly Arg Lys Val Thr Phe
    290                 295                 300

Phe Glu Pro Gly Ser Gly Asp Glu Asn Gly Thr Ser Asn Lys Glu Asp
305                 310                 315                 320

Glu Phe Arg Met Pro Tyr Leu Ser His Gln Gln Leu Pro Ala Gly Ile
                325                 330                 335

Leu Pro Met Val Pro Glu Val Ala Gln Ala Val Gly Val Ser Gln Gly
                340                 345                 350

His His Thr Lys Asp Phe Thr Arg Ala Ala Pro Asn Pro Ala Lys Ala
                355                 360                 365

Thr Val Thr Ala Met Ile Ala Arg Glu Leu Leu Tyr Gly Gly Thr Ser
    370                 375                 380

Pro Thr Ala Glu Thr Ile Leu Lys Asn Asn Ile Ser Ser Gly His Val
385                 390                 395                 400

Pro His Gly Pro Leu Thr Arg Pro Ser Glu Gln Leu Asp Tyr Leu Ser
                405                 410                 415

Arg Val Gln Gly Phe Gln Val Glu Tyr Lys Asp Phe Pro Lys Asn Asn
                420                 425                 430

Lys Asn Glu Phe Val Ser Leu Ile Asn Cys Ser Ser Gln Pro Pro Leu
                435                 440                 445

Ile Ser His Gly Ile Gly Lys Asp Val Glu Ser Cys His Asp Met Ala
                450                 455                 460

Ala Leu Asn Ile Leu Lys Leu Leu Ser Glu Leu Asp Gln Gln Ser Thr
465                 470                 475                 480

Glu Met Pro Arg Thr Gly Asn Gly Pro Met Ser Val Cys Gly Arg Cys
                485                 490                 495

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
gcctgggagg ggtggtggcc attttttg                                    28

<210> SEQ ID NO 4
<211> LENGTH: 26
<212> TYPE: DNA
```

```
<213> ORGANISM: Artificial Sequence
<220> FEATURE:
<223> OTHER INFORMATION: Primer

<400> SEQUENCE: 4
gtttgctcta gaatgaacgg tggaag                                            26

<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
cacctccagc ctctctggca ggggctc                                           27

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
ggcaaaggaa agacaagaca tggctgcg                                          28

<210> SEQ ID NO 7
<211> LENGTH: 13
<212> TYPE: PRT
<213> ORGANISM: Artificial Sequence
<220> FEATURE:
<223> OTHER INFORMATION: Peptide

<400> SEQUENCE: 7

Cys Met Ala Pro Val Lys Lys Leu Val Val Lys Gly Gly
  1               5                  10

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
atcgcttctc ggccttttt                                                    18

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gggtgcaccg ttcctggga                                                    19

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
```

```
gactatactt tcagggatca tttc                                              24
```

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11

```
ccactcagac cgcgttctct c                                                 21
```

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12

```
gtgcctgtag tcccagctac                                                   20
```

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13

```
gagacggggt ctcgctatg                                                    19
```

<210> SEQ ID NO 14
<211> LENGTH: 17
<212> TYPE: DNA
<213> ORGANISM: Artificial Sequence
<220> FEATURE:
<223> OTHER INFORMATION: Primer

<400> SEQUENCE: 14

```
ggaaggtctg agactag                                                      17
```

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15

```
atctcctgcc cagtctg                                                      17
```

<210> SEQ ID NO 16
<211> LENGTH: 73
<212> TYPE: PRT
<213> ORGANISM: Homo sapiens
<220> FEATURE:
<221> NAME/KEY: BINDING
<222> LOCATION: (0)...(0)

<400> SEQUENCE: 16

```
Leu Asn Lys Ser Glu Leu Ser Gln Val Phe Glu Ile Ala Leu Lys Arg
 1               5                  10                  15

Asn Leu Pro Val Asn Phe Glu Val Ala Arg Glu Ser Gly Pro Pro His
            20                  25                  30
```

```
Met Lys Asn Phe Val Thr Lys Val Ser Val Gly Glu Phe Val Gly Glu
        35                  40                  45

Gly Glu Gly Lys Ser Lys Ile Ser Lys Lys Asn Ala Ala Ile Ala
    50                  55                  60

Val Leu Glu Glu Leu Lys Lys Leu Pro
65                  70

<210> SEQ ID NO 17
<211> LENGTH: 73
<212> TYPE: PRT
<213> ORGANISM: Drosophila melanogaster
<220> FEATURE:
<221> NAME/KEY: BINDING
<222> LOCATION: (0)...(0)

<400> SEQUENCE: 17

Lys Asp Lys Thr Pro Met Cys Leu Val Asn Glu Leu Ala Arg Tyr Asn
1               5                   10                  15

Lys Ile Thr His Gln Tyr Arg Leu Thr Glu Arg Gly Pro Ala His
            20                  25                  30

Cys Lys Thr Phe Thr Val Thr Leu Met Leu Gly Asp Glu Glu Tyr Ser
        35                  40                  45

Ala Asp Gly Phe Lys Ile Lys Lys Ala Gln His Leu Ala Ala Ser Lys
    50                  55                  60

Ala Ile Glu Glu Thr Met Tyr Lys His
65                  70

<210> SEQ ID NO 18
<211> LENGTH: 72
<212> TYPE: PRT
<213> ORGANISM: Drosophila melanogaster
<220> FEATURE:
<221> NAME/KEY: BINDING
<222> LOCATION: (0)...(0)

<400> SEQUENCE: 18

Asp Lys Lys Ser Pro Ile Ser Gln Val His Glu Ile Gly Ile Lys Arg
1               5                   10                  15

Asn Met Thr Val His Phe Lys Leu Arg Glu Glu Gly Pro Ala His Met
            20                  25                  30

Lys Asn Phe Ile Thr Ala Cys Ile Val Gly Ser Ile Val Thr Glu Gly
        35                  40                  45

Glu Gly Asn Gly Lys Lys Val Ser Lys Lys Arg Ala Ala Glu Lys Met
    50                  55                  60

Leu Val Glu Leu Gln Lys Leu Pro
65                  70

<210> SEQ ID NO 19
<211> LENGTH: 74
<212> TYPE: PRT
<213> ORGANISM: Homo sapiens
<220> FEATURE:
<221> NAME/KEY: BINDING
<222> LOCATION: (0)...(0)

<400> SEQUENCE: 19

Gln Gly Ile Asn Pro Ile Ser Arg Leu Ala Gln Ile Gln Gln Ala Lys
1               5                   10                  15

Lys Glu Lys Glu Pro Glu Tyr Thr Leu Leu Thr Glu Arg Cys Leu Pro
            20                  25                  30

Arg Arg Arg Glu Phe Val Met Gln Val Lys Val Gly Asn His Thr Ala
```

```
              35                  40                  45
Glu Gly Thr Cys Thr Asn Lys Val Ala Lys Ala Asn Ala Ala Glu
     50                  55                  60

Asn Met Leu Glu Ile Leu Gly Phe Lys Val
65                  70

<210> SEQ ID NO 20
<211> LENGTH: 75
<212> TYPE: PRT
<213> ORGANISM: Drosophila melanogaster
<220> FEATURE:
<221> NAME/KEY: BINDING
<222> LOCATION: (0)...(0)

<400> SEQUENCE: 20

Asp Ala Asp Asn Pro Ile Thr Lys Leu Ile Gln Leu Gln Gln Thr Arg
1               5                  10                  15

Lys Glu Lys Glu Pro Ile Phe Glu Leu Ile Ala Lys Asn Gly Asn Glu
             20                  25                  30

Thr Ala Arg Arg Arg Glu Phe Val Met Glu Val Ser Ala Ser Gly Ser
         35                  40                  45

Thr Ala Arg Gly Thr Gly Asn Ser Lys Lys Leu Ala Lys Arg Asn Ala
     50                  55                  60

Ala Gln Ala Leu Phe Glu Leu Leu Glu Ala Val
65                  70                  75

<210> SEQ ID NO 21
<211> LENGTH: 21
<212> TYPE: PRT
<213> ORGANISM: Homo sapiens
<220> FEATURE:
<221> NAME/KEY: BINDING
<222> LOCATION: (0)...(0)

<400> SEQUENCE: 21

Gly Lys Gly Lys Thr Arg Gln Ala Ala Lys His Asp Ala Ala Ala Lys
1               5                  10                  15

Ala Leu Arg Ile Leu
             20

<210> SEQ ID NO 22
<211> LENGTH: 21
<212> TYPE: PRT
<213> ORGANISM: Homo sapiens
<220> FEATURE:
<221> NAME/KEY: BINDING
<222> LOCATION: (0)...(0)

<400> SEQUENCE: 22

Gly Ile Gly Lys Asp Val Glu Ser Cys His Asp Met Ala Ala Leu Asn
1               5                  10                  15

Ile Leu Lys Leu Leu
             20

<210> SEQ ID NO 23
<211> LENGTH: 21
<212> TYPE: PRT
<213> ORGANISM: Drosophila melanogaster
<220> FEATURE:
<221> NAME/KEY: BINDING
<222> LOCATION: (0)...(0)

<400> SEQUENCE: 23
```

-continued

```
Gly Ile Gly Arg Thr Leu Gln Gln Ala Lys His Asp Ala Ala Arg
1               5                   10                  15

Ala Leu Gln Val Leu
            20

<210> SEQ ID NO 24
<211> LENGTH: 21
<212> TYPE: PRT
<213> ORGANISM: Drosophila melanogaster
<220> FEATURE:
<221> NAME/KEY: BINDING
<222> LOCATION: (0)...(0)

<400> SEQUENCE: 24

Gly Val Gly Lys Ser Ser Glu Glu Ser Gln Asn Asp Ala Ala Ser Asn
1               5                   10                  15

Ala Leu Lys Ile Leu
            20
```

TELOMERASE-ASSOCIATED PROTEINS

CROSS REFERENCE TO RELATED APPLICATIONS

This application claims priority from U.S. Provisional Application Ser. No. 60/080,783, filed on Apr. 6, 1998.

STATEMENT AS TO FEDERALLY SPONSORED RESEARCH

Funding for the work described herein was provided in part by the federal government, which has certain rights in the invention.

TECHNICAL FIELD

The invention relates to a human staufen polypeptide that is associated with telomerase.

BACKGROUND OF THE INVENTION

Telomerase is a specialized ribonucleoprotein (RNP) reverse transcriptase that is essential for telomere maintenance. Telomerase uses an internal RNA template to synthesize telomeric repeat sequences onto chromosome ends. Deletion of the essential RNA component of telomerase leads to progressive telomere shortening, chromosome instability and cell death in both yeast and mouse cells. This multi-subunit enzyme is regulated at several levels in human cells.

The telomerase enzyme is made up of an essential core as well as several accessory proteins. The core telomerase consists of the RNA component (Telomerase RNA, TR) and the catalytic subunit (Telomerase Reverse Transcriptase, TERT). The structure of the RNA component is conserved in ciliates, in which the RNA is 150–200 nucleotides (nt) in length. In mammalian cells, the RNA component is significantly larger, 390–450 nt. Feng, J. et al., *Science*, 1995, 269:1236–1241. The catalytic TERT component, first identified in the ciliate Euplotes, has homologues in yeast (EST 2), human (hTERT), and mouse (mTERT). TERT contains sequence motifs similar to reverse transcriptase and mutations of essential aspartate residues that are conserved in the catalytic triad of reverse transcriptases eliminates telomerase activity. Minimal telomerase activity can be reconstituted in an in vitro transcription/translation extract using TERT and TR components, indicating that these are sufficient for catalysis. Weinrich, S. L. et al., *Nat. Genet.*, 1997, 17:498–502.

Both telomere length and telomerase activity have been implicated in cellular senescence and cancer. In most somatic cells, telomerase activity is not detected and telomeres shorten with each division. Allsopp, R. C. et al., *Proc. Natl. Acad. Sci. USA*, 1992, 89:1014–1018. Artificial elongation of telomeres by ectopic hTERT expression in primary human cells leads to telomere elongation and a bypass of cellular senescence, suggesting that telomere shortening may trigger cellular senescence in primary human cells. During immortalization of mammalian cells in culture, telomerase is activated, telomere length is stabilized, and cells continue to proliferate, suggesting that telomerase activation and telomere stabilization are required for the long term growth of cancer cells. Telomerase activity is present in the vast majority of human tumors while little activity is found in the normal tissues from which the tumors were derived. Together, these data lead to the proposal that telomerase inhibition may inhibit tumor growth. See, for example, Harley, C. B. et al., *Cold Spring Harbor Symp. Quant. Biol.*, 1994, 59:307–315.

New evidence also indicates that telomerase plays a role in tumor initiation, not just in long term tumor growth. Telomerase null mice with significantly shortened telomeres show an increased rate of tumor formation with age compared with wild-type mice, suggesting loss of telomere function leads to increased genetic instability. Furthermore, in cells lacking the p53 gene, absence of telomerase increased the rate of focus formation after transfection of myc and RAS. This suggests that the absence of both telomerase and p53 cooperated to increase genetic instability that leads to tumor initiation. Thus, characterization of telomerase and its associated components is important to understanding tumor formation.

SUMMARY OF THE INVENTION

The invention is based on the identification of telomerase-associated proteins that bind telomerase RNA and that may play a role in telomerase assembly, transport, and regulation. As described herein, human staufen (hStau) polypeptide and ribosomal associated protein L22 bind human telomerase RNA and are associated with telomerase activity in vivo.

In one aspect, the invention features an isolated human staufen polypeptide, wherein the polypeptide includes an amino acid sequence substantially identical to the amino acid sequence of about residue 49 to about residue 496 of SEQ ID NO:2. For example, the polypeptide can be substantially identical to the amino acid sequence of SEQ ID NO:2. The polypeptide also can be, for example, the amino acid sequence of SEQ ID NO:2 or the amino acid sequence of about residue 49 to about residue 496 of SEQ ID NO:2. Polypeptides that include the amino acid sequence of SEQ ID NO:2 can have a molecular weight of approximately 55 kDa. Polypeptides of the invention bind RNA. For example, the polypeptide can bind double-stranded RNAs such as telomerase RNA. The polypeptide can be in a complex with the catalytic subunit of telomerase.

The invention also features an isolated polynucleotide encoding a human staufen polypeptide. The encoded polypeptide can include an amino acid sequence substantially identical to the amino acid sequence of about residue 49 to about residue 496 of SEQ ID NO:2. For example, the polypeptide can include the amino acid sequence of SEQ ID NO:2. The polynucleotide can have a nucleotide sequence at least 70%, 80%, 90%, or 95% identical to the nucleotide sequence of SEQ ID NO:1.

Polynucleotides of the invention also can be at least 150 nucleotides in length and hybridize under stringent conditions to the nucleotide sequence of SEQ ID NO:1 or the complement thereof. For example, the polynucleotide can include the nucleotide sequence of SEQ ID NO:1.

In another aspect, the invention features an antibody having specific binding affinity for a human staufen polypeptide that includes, for example, the amino acid sequence of SEQ ID NO:2. The antibody can be polyclonal or monoclonal.

The invention also features a method for inhibiting telomerase activity. The method includes administering to a cell an amount of an agent effective to inhibit the interaction between a telomerase-associated polypeptide and telomerase. The telomerase-associated polypeptide can be, for example, human staufen polypeptide or ribosomal associated protein L22.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIGS. 1A and 1B are a structural alignment of hStau (TEP3) and other double stranded (ds) RNA binding proteins (1A) and a sequence comparison of domains in hStau and Drosophila Staufen (dSTAU) (1B). In FIG. 1A, full length dsRNA binding domains are indicated by gray boxes and short domains by white boxes. Numbers under the domains in hStau and dSTAU correspond to the sequences listed in FIG. 1B. In the top panel of FIG. 1B, alignments of full length domains are shown. The bottom panel shows alignment of short domains. Identical residues are shaded. Asterisks (*) indicate the residues that are most highly conserved in all of the in the ds RNA binding domain containing proteins. Sequences used in the alignment are: hStau 1, aa 59 79 (TEP3-1)(SEQ ID NO:16); hStau 2, aa 100 172 (TEP3-2) (SEQ ID NO:17); hStau 3, aa 202 275 (TEP3-3)(SEQ ID NO:18); hStau 4, aa 452 472 (TEP3-4) (SEQ ID NO:19); dSTAU 1, aa 308 380 (SEQ ID NO:20); dSTAU 2, 490 559(SEQ ID NO:21); dSTAU 3, 575 647 (SEQ ID NO:22); dSTAU 4, aa 708 782 (SEQ ID NO:23); and dSTAU 5, aa 948 1020 (SEQ ID NO:24).

FIG. 2A is a Western blot analysis of 293 cell extract (lane 1) and hStau immunoprecipitates (lane 2) using anti-hStau antibody, that shows a 55 kD hStau protein. FIG. 2B is Western blot analysis of 293 cell extracts (lane 1) and L22 immunoprecipitates using pre-immune serum (lane 2), anti-L22 serum (lane 3), and using anti-L22 serum preincubated with L22 peptide before immunoprecipitation. Arrow indicates the L22 band (15 kD). The relative mobilities of molecular weight markers (in kD) are indicated to the left in FIGS. 2A–2B.

In FIG. 3A, telomerase assays were carried out on 293 extract (lane 1) and immunoprecipitation pellets (lanes 2–13) from immunoprecipitations with various antibodies. Lanes 2 and 3, precipitation with hStau pre-immune serum; lanes 4 and 5, precipitation with anti-hStau antibody; lanes 6 and 7, precipitation with anti-GST antibody; lanes 8 and 9 precipitation with L22 pre-immune serum; lanes 10 and 11, precipitation with anti-L22 antibody; and lanes 12 and 13, precipitation with anti-L22 antibody pre-incubated with L22 peptides. Samples in lanes 3, 5, 7, 9, 11, and 13 were pretreated with RNase before telomerase reactions. Arrow indicates the location of the internal control (IC) for PCR amplification.

FIG. 3B is a Western blot analysis using anti-HA antibody on cell lysate (lanes 1 and 2) or various immunoprecipitation pellets (lanes 3–8). Extracts for lanes 1, 3, and 6 were mock transfected 293 extract, and were hTERT-HA transfected cell extract for lanes 2, 4, 5, 7, and 8. Antibodies used in immunoprecipitation reactions were: lanes 3 and 5, anti-L22; lane 4, L22 pre-immune serum; lanes 6 and 8, anti-hStau; lanes 7, hStau pre-immune serum. The relative mobility of molecular weight markers (in kD) are indicated to the left. Arrow indicates the hTERT-HA tagged band.

FIG. 5A indicates that hStau and L22 do not interact with each other. 293 cell lysate was immunoprecipitated with hStau pre-immune serum (lane 2), hStau antibody (lane 3), L22 pre-immune serum (lane 4), or L22 antibody (lane 5). Pellet fractions were analyzed by western hybridization, and probed with either hStau antibody (upper panel) or L22 antibody (lower panel). FIG. 5B indicates that hStau and myc-TEP1 do not interact. 293 cells were either mock transfected (lanes 1, 3, and 4) or transfected with myc-TEP1 construct (lanes 2, 5, and 6), and cell lysates were either run directly on a western blot (lanes 1 and 2) or immunoprecipitated with either hStau pre-immune serum (lanes 3 and 5) or hStau antibody (lanes 4 and 6). The western blot was probed with anti-myc antibody (upper panel) or hStau antibody (lower panel). FIG. 5C indicates that L22 and myc-TEP1 do not interact. 293 cells were either mock transfected (lanes 1 and 3) or transfected with myc-TEP1 construct (lanes 2, 4, and 5), and cell lysates were either run directly on a western blot (lanes 1 and 2) or immunoprecipitated with either hStau pre-immune serum (lane 4) or L22 antibody (lanes 3 and 5). The western blot was probed with anti-myc antibody (upper panel) or L22 antibody (lower panel).

DETAILED DESCRIPTION

Figure 1A:
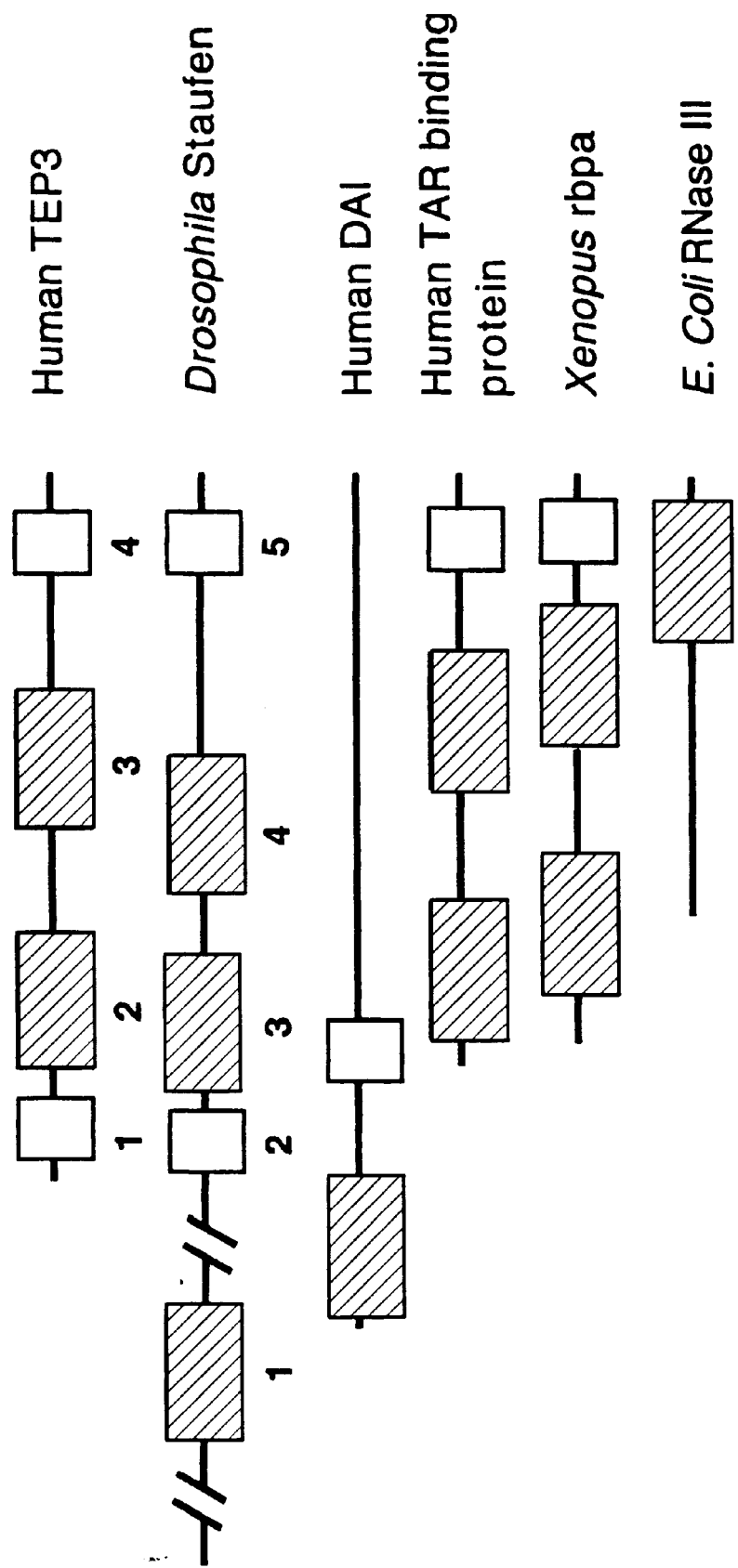

The invention relates to human staufen (hStau) polypeptides, as well as polynucleotides encoding hStau polypeptides, antibodies having specific binding affinity for hStau polypeptides, and methods for using hStau and other telomerase-associated proteins to inhibit telomerase activity.

As described herein, hStau is a specific double stranded RNA binding protein that is specifically associated with human telomerase RNA (hTR) in vivo, and can be classified with a family of proteins that contain multiple double stranded RNA binding domains. The structural organization of the RNA binding domains of hStau, as well as sequences within these domains, are most similar to the domains of Staufen protein from Drosophila. See, St. Johnston, D. et al., *Cell*, 1991, 66(1):51–63. In Drosophila, staufen specifically binds bicoid and oskar mRNA, and is necessary for the proper localization of these RNAs to the anterior and posterior of the oocyte, respectively. Drosophila staufen also binds to prospero mRNA and contributes to its localization to neuroblasts during development. In vitro, staufen binds directly to bicoid mRNA. In fact, a 76 amino acid fragment containing the double stranded RNA binding domain of Drosophila staufen is sufficient to bind RNAs that contain extensive secondary structure, such as U1, U2, and VA1, but not unstructured RNAs. See, St. Johnston, D. et al., *Proc. Natl. Acad. Sci. USA*, 1992, 89(22):10979–10983. Although Drosophila staufen appears to bind structured RNA with little specificity in vitro, RNA binding proteins do have higher affinity for their specific target in vivo. For example, hStau binds hTR as well as U2 and U3 snRNAs in vivo, but has no detectable association with 7SL or RNase P RNAs in vivo. Since hTR only is present at about 500 copies per cell, these results suggest that hStau proteins bind hTR in vivo. In vivo binding specificity may be achieved, at least in part, through conformation of the RNA and/or the association with other proteins in a RNP complex.

Human Staufen Polypeptides

The invention features an isolated hStau polypeptide that includes the amino acid sequence of SEQ ID NO:2 and fragments thereof, as well amino acid sequences that are substantially identical to SEQ ID NO:2 or fragments thereof. For example, a hStau polypeptide can include about residue 49 to about residue 496 of SEQ ID NO:2. The term "polypeptide" includes any chain of amino acids, regardless of length or post-translational modification. "Substantially identical" amino acid sequences include the referenced amino acid sequence, as well as sequences that contain substitutions in the amino acid sequence of SEQ ID NO:2 that retain the capacity to bind RNA. In general, conservative amino acid substitutions, i.e., substitutions of similar amino acids, are tolerated without affecting protein function. Similar amino acids can be those that are similar in size and/or charge properties. For example, aspartate and glutamate and isoleucine and valine are both pairs of similar amino acids. Similarity between amino acid pairs has been assessed in the art in a number of ways. Dayhoff et al., *Atlas of Protein Sequence and Structure*, 1978, 5(3):345–352, provides frequency tables for amino acid substitutions which can be employed as a measure of amino acid similarity.

Isolated hStau polypeptides of the invention can be obtained in various ways, including by recombinant expression, purification from a biological sample or cell lysate, or chemical synthesis, and are free of components that naturally accompany it.

Recombinant hStau can be produced by ligating a nucleic acid sequence encoding hStau or a fragment thereof into a nucleic acid construct such as an expression vector, and transforming a bacterial or eukaryotic host cell with the expression vector. In general, nucleic acid constructs include a regulatory sequence operably linked to a hStau nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include without limitation the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express hStau. A nucleic acid encoding hStau can be cloned into, for example, a baculoviral vector and then used to transfect insect cells. Alternatively, the nucleic acid encoding hStau can be introduced into a SV40, retroviral or vaccinia based viral vector and used to infect host cells.

Mammalian cell lines that stably express hStau can be produced by using expression vectors with the appropriate control elements and a selectable marker. For example, the eukaryotic expression vector pCDNA.3.1$^+$ (Invitrogen, San Diego, Calif.) is suitable for expression of hStau in, for example, COS cells or HEK293 cells. Following introduction of the expression vector by electroporation, DEAE dextran, or other suitable method, stable cell lines can be selected. Alternatively, transiently transfected cell lines are used to produce hStau. Human Staufen also can be transcribed and translated in vitro using wheat germ extract or rabbit reticulocyte lysate.

Human Staufen polypeptide also can be purified from a biological sample or cell lysate using standard protein purification techniques such as affinity chromatography, gel-filtration, and ion-exchange chromatography. hStau activity can be assessed during purification by determining, for example, binding of RNA, and in particular, of hTR.

The invention also features isolated complexes of hStau and the catalytic subunit of telomerase. In reference to complexes, the term "isolated" refers to a complex that is free of cellular debris. Complexes of hStau and the catalytic subunit of telomerase can be isolated by methods described herein. For example, an antibody having specific binding affinity for hStau can be used to immunoprecipitate complexes of the invention. Alternatively, isolated complexes can be formed in vitro upon incubation of hStau and the catalytic subunit of telomerase. The catalytic subunit of telomerase (TERT) can be from yeast, human, or mouse. The DNA and amino acid sequences of the catalytic subunits from various organisms are available on GenBank.

Human Staufen Nucleic Acid Sequences

The invention also features isolated polynucleotides encoding a hStau polypeptide. As used herein, "isolated" refers to a sequence corresponding to part or all of the hStau gene, but free of sequences that normally flank one or both sides of the hStau gene in a mammalian genome. An isolated polynucleotide can be, for example, a recombinant DNA molecule, provided one of the nucleic acid sequences normally found immediately flanking that recombinant DNA molecule in a naturally-occurring genome is removed or absent. Thus, isolated polynucleotides include, without limitation, a recombinant DNA that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated polynucleotide can include a recombinant DNA molecule that is part of a hybrid or fusion polynucleotide.

It will be apparent to those of skill in the art that a polynucleotide existing among hundreds to millions of other polynucleotides within, for example, cDNA or genomic libraries, or gel slices containing a genomic DNA restriction digest is not to be considered an isolated polynucleotide.

"Polynucleotides" are at least about 14 nucleotides in length. For example, the polynucleotide can be about 14 to 20, 20–50, 50–100, or greater than 150 nucleotides in length. Polynucleotides can be DNA or RNA, linear or circular, and in sense or antisense orientation. For example, hStau polynucleotides can encode a polypeptide that includes the amino acid sequence of SEQ ID NO:2 or fragments thereof, or amino acid sequences substantially identical to such sequences. For example, the polynucleotide can encode a polypeptide having the amino acid sequence of about residue 49 to about residue 496 of SEQ ID NO:2.

Polynucleotides having a nucleotide sequence other than the nucleotide sequence of SEQ ID NO:1 also can encode hStau polypeptides. The degeneracy of the genetic code is well-known in the art; i.e., for many amino acids, there is more than one nucleotide triplet that serves as the codon for the amino acid. In addition, conservative amino acid substitutions can be introduced in the hStau polypeptide, as discussed above.

In certain embodiments, polynucleotides of the invention have at least 70% sequence identity to the nucleotide sequence of SEQ ID NO:1. The nucleic acid sequence can have, for example, at least 80%, 90%, or 95% sequence identity to SEQ ID NO:1. Generally, percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Nucleic acid sequences can be aligned by visual inspection, or by using sequence alignment software. For example, MEGA-LIGN® (DNASTAR, Madison, Wis., 1997) sequence alignment software, using default parameters for the Clustal algorithm, can be used to align polynucleotides. In this method, sequences are grouped into clusters by examining the distance between all pairs. Clusters are aligned as pairs, then as groups.

The invention also features polynucleotides that are at least 150 nucleotides in length and that hybridize under stringent conditions to the hStau polynucleotide of SEQ ID NO:1 or to the complement thereof. For example, the polynucleotide can include nucleotide 1 to about nucleotide 614 of SEQ ID NO:1, nucleotide 518 to nucleotide 3220 of SEQ ID NO:1, or nucleotides 1 to 3190 of SEQ ID NO:1. Hybridization typically involves Southern analysis (Southern blotting). See, for example, sections 9.37–9.52 of Sambrook et al., 1989, "Molecular Cloning, A Laboratory Manual", second edition, Cold Spring Harbor Press, Plainview; N.Y. Stringent conditions can include the use of low ionic strength and high temperature for washing, for example, 0.015 M NaCl/0.0015 M sodium citrate (0.1× SSC), 0.1% sodium dodecyl sulfate (SDS) at 60° C. Alternatively, denaturing agents such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

Human Staufen polynucleotides of the invention can be cloned from a cDNA library, such as a human testis cDNA library, or can be obtained by other means including chemical synthesis and polymerase chain reaction (PCR) technology using oligonucleotide pairs such as 5'-GCC TGG GAG GGG TGG TGG CCA TTT TTT G-3' (SEQ ID NO:3) and 5'-GTT TGC TCT AGA ATG AAC GGT GGA AG-3' (SEQ ID NO:4). PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplified. See, for example, Lewis, R. *Genetic Engineering News*, 12(9):1 (1992); Guatelli et al., *Proc. Natl. Acad. Sci. USA*, 87:1874–1878 (1990); and Weiss, R., *Science*, 254:1292 (1991).

Human Staufen Antibodies

Antibodies having specific binding affinity for human staufen polypeptide can be produced through standard methods. As used herein, the term "antibody" includes polyclonal antibodies, monoclonal antibodies, humanized or chimeric antibodies, single chain antibodies, Fab fragments, and $F(ab)_2$ fragments. In general, hStau can be produced in various ways, including recombinantly, or can be purified from a biological sample or cell lysate, and used to immunize animals.

Various host animals can be immunized by injection of an hStau polypeptide. Host animals include, for example, rabbits, chickens, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin (KLH), and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a hStau polypeptide and standard hybridoma technology. In particular, monoclonal antibodies can be obtained by any technique that provides for the production of antibody molecules by continuous cell lines in culture such as described by Kohler, G. et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77–96 (1983)). Such antibodies can be of any immunoglobulin class including IgG, IgM, IgE, IgA, IgD, and any subclass thereof. The hybridoma producing the monoclonal antibodies of the invention can be cultivated in vitro and in vivo.

A chimeric antibody is a molecule in which different portions are derived from different animal species, such as those having a variable region derived from a murine monoclonal antibody and a human immunoglobulin constant region. Chimeric antibodies can be produced through standard techniques.

Single chain antibodies are formed by linking the heavy and light chain fragments of the Fv region via an amino acid bridge, resulting in a single chain polypeptide. Single chain antibodies can be produced through standard techniques. See, for example, U.S. Pat. No. 4,946,778.

Antibody fragments that have specific binding affinity for hStau polypeptide can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed. See, for example, Huse et al., *Science*, 246:1275 (1989). Once produced, antibodies or fragments thereof are tested for recognition of hStau by standard immunoassay methods including ELISA techniques, radioimmunoassays and Western blotting. See, *Short Protocols in Molecular Biology*, Chapter 11, Green Publishing Associates and John Wiley & Sons, Edited by Ausubel, F. M et al., 1992.

Methods for Inhibiting Telomerase Activity

The invention also provides methods for inhibiting telomerase activity. As described herein, ribosomal associated protein L22 and hStau both are RNA binding proteins that are associated with human telomerase complexes. Although both of these proteins are associated with hTR in vivo, they appear not to associate with each other. This suggests that hTR is present in multiple complexes in the cell and these distinct complexes may represent different stages of RNP assembly. RNA binding proteins may be critically involved in the maturation, localization, and assembly of the telomerase RNP. Thus, inhibition of the binding of the telomerase-associated proteins to the telomerase RNA may inhibit telomerase activity.

In general, telomerase activity can be inhibited by administering to a cell an amount of an agent effective to inhibit the interaction of a telomerase-associated polypeptide with a telomerase RNA. An agent can be a biological macromolecule such as an oligonucleotide or a polypeptide, a chemical compound, a mixture of chemical compounds, or an extract isolated from bacterial, plant, fungal, or animal matter.

A suitable polypeptide can be a telomerase-associated polypeptide. For example, an effective amount of a telomerase-associated polypeptide can bind the telomerase RNA such that the active telomerase core can not be formed. Thus, the polypeptide would titrate the telomerase RNA away from the catalytic component, and telomerase would be inhibited. The telomerase-associated polypeptide can include, for example, the RNA binding domains of hStau or L22. For example, a suitable hStau polypeptide can include RNA binding domains 1, 2, 3, or 4, or combinations thereof. RNA binding domains 1, 2, 3, and 4 of hStau include amino acids 59–79, 100–172, 202–275, and 452–472 of SEQ ID NO:2, respectively.

Suitable oligonucleotides can be RNA or DNA based nucleic acids including chimeric mixtures, derivatives, and modified versions thereof. The oligonucleotide can be modified at the base moiety, sugar moiety, or phosphate backbone, for example, to improve stability of the molecule or hybridization. A modified phosphate backbone can include, for example, phosphorothioate, phosphorodithioate, phosphoramidothioate, phosphoramidate, phosphordiamidate, methylphosphonate, alkyl phosphotriester, formacetel linkages, or analogs thereof. An oligonucleotide also can be a peptide nucleic acid, an uncharged nucleic acid derivative, which contains a pseudopeptide backbone. Peptide nucleic acids can be produced using standard techniques. See, for example, U.S. Pat. No. 5,539,082.

For example, an oligonucleotide can be an antisense oligonucleotide, i.e., complementary to at least a portion of a target RNA, to the coding sequence or transcribed untranslated region of a telomerase-associated polypeptide such as hStau or L22. Antisense oligonucleotides can be full-length or less than full-length. Antisense oligonucleotides that are less than full-length are typically at least 6 nucleotides in length, e.g., from 6 to about 200 nucleotides in length. The term "complementary" refers to a sequence that is able to hybridize with the RNA, forming a stable duplex under normal in vivo conditions. The ability to hybridize depends on both the degree of complementarily and the length of the antisense nucleic acid. Generally, the longer the hybridizing nucleic acid, the more base mismatches with an RNA it may contain and still form a stable duplex. One skilled in the art can ascertain a tolerable degree of mismatch by use of standard procedures to determine the melting point of the hybridized complex. Administration of an effective amount of such antisense oligonucleotides would prevent expression of telomerase-associated polypeptides, and inhibit telomerase activity.

Alternatively, an oligonucleotide can include an RNA binding site recognized by the telomerase-associated polypeptide. Administration of an effective amount of such an oligonucleotide provides the cell with an excess of the oligonucleotide. Consequently, telomerase-associated polypeptides bind the oligonucleotide rather than the telomerase RNA, and telomerase activity is inhibited. The binding specificity of L22 includes a stem loop structure with three conserved nucleotides at the top of the stem. Dobbelstein, M. et al., *J. Virol.*, 1995, 69(12):8027–8034.

Oligonucleotides can be synthesized by standard methods known in the art, e.g., by use of an automated nucleic acid synthesizer (such as those commercially available from Biosearch, Applied Biosystems). Phosphorothioate oligonucleotides can be synthesized by the method of Stein et al., *Nucl. Acids Res.*, 1988, 16:3209–3221. Methylphosphonate oligonucleotides can be prepared by use of controlled pore glass polymer supports, as described by Sarin et al., *Proc. Natl. Acad. Sci. USA*, 1988, 85(20):7448–7451.

In addition, ribozyme molecules can be designed to catalytically cleave telomerase-associated polypeptide transcripts, preventing expression of the telomerase-associated polypeptides. Various ribozymes that cleave RNA can be used. For example, hammerhead ribozymes cleave RNAs at locations dictated by flanking regions that form complementary base pairs with the target RNA. The sole requirement is that the target RNA have the following sequence of two bases: 5'-UG-3'. The construction and production of hammerhead ribozymes is known in the art. See, for example, U.S. Pat. No. 5,254,678. Alternatively, RNA endoribonucleases such as the one that occurs naturally in *Tetrahymena thermophila* can be used. See, for example, U.S. Pat. No. 4,987,071.

Oligonucleotides and ribozymes can be delivered to a cell in vivo by a number of methods. For example, oligonucleotides can be injected directly into the tissue site, e.g., a tumor, or can be administered systemically. Alternatively, recombinant DNA constructs can be used to express oligonucleotides, ribozymes, and telomerase-associated polypeptides of the invention. For example, a vector can be introduced in vivo such that it is taken up by a cell and directs the transcription of the oligonucleotide, ribozyme, or polypeptide. Vectors can remain episomal or can integrate into a chromosome, and are produced by standard recombinant DNA technology.

Inhibiting agents (other than antisense oligonucleotides) can be identified using an in vitro system. For example, telomerase activity can be reconstituted in vitro with telomerase RNA and TERT, the catalytic component of telomerase, in the presence of telomerase-associated polypeptides. See, Weinrich, R. L. et al., *Nat. Genet.*, 1997, 17:498–502; and Beattie, T. L. et al., *Curr. Biol.*, 1998, 8:177–180 for a description of reconstitution of telomerase. Various agents can be added to the reaction, and telomerase activity is monitored with standard procedures. See, Kim, N. W. and Wu, F., *Nucl. Acids Res.*, 1997, 25:2595–2597 for a telomeric repeat amplification protocol (TRAP) for detecting telomerase activity.

A cell-based system also can be used to identify inhibiting agents. Agents to be screened can be administered to a cell, as discussed above, and telomerase activity then is monitored in the presence and absence of the agents. Cells suitable for screening express the telomerase-associated polypeptides and contain detectable telomerase activity.

The invention will be further described in the following examples, which do not limit the scope of the invention described in the claims.

EXAMPLES

Example 1

Materials and methods
Identification of Telomerase RNA Binding Proteins

A three hybrid system was modified and used to screen for hTR binding proteins. Nucleotides 64–222 of hTR were fused to MS2 phage DNA to generate pLS112 plasmid, which also contains ura3. The sequence of hTR can be obtained under GenBank Accession No. U86046 S79400. To avoid transcriptional termination by the RNase P RNA polymerase III, four nucleotides in hTR-MS2 RNA were changed. Positions 82, 83, 102, and 103 were changed to A, A, A, C, respectively, to disrupt a string of uridines which was observed to cause transcriptional termination in preliminary experiments. The fusion RNA was detected on Northern blots, indicating it was transcribed and stable in yeast cells. The pLS112 plasmid was transformed into a modified yeast reporter strain (L40coatng) along with cDNA-GAD libraries from HeLa, Jurket, or human testes (provided by Dr. G. Hannon, Dr. L. VanAelst, and Clontech Inc., Palo Alto, Calif.). See, SenGupta, D. J. et al., *Proc. Natl. Acad. Sci. USA*, 1996, 93(16):8496–8501 for a description of yeast reporter strain L40. Positive clones that grew in the presence of 5 mM 3-aminotriazole (3 AT) and that stained positive for β-galactosidase were picked. These clones were tested for reporter gene activation in the absence of RNA plasmids, and only clones which activated in the presence of the hTR-MS2 RNA were characterized further. Positive clones from this screen were characterized further by DNA sequencing and expression in mammalian cells.

Cloning of hStau cDNA

Rapid amplification of cDNA ends (RACE) polymerase chain reaction (PCR) was used to clone hStau. Using a tagged human testis cDNA library (Marathon ready human testis cDNA from Clontech) and gene specific primers within the cloned region, both the 5' and 3' halves of the gene were amplified by PCR, according to manufacture protocols, using AP1 and hStau specific primers 10-9 5'-CAC CTC CAG CCT CTC TGG CAG GGG CTC-3' (SEQ ID NO:5), and 10-10 5'-GGC AAA GGA AAG ACA AGA CAT GGC TGC G-3' (SEQ ID NO:6). Each half was subcloned into pCRScript SK+ and sequenced. The 5' fragment contained nucleotides 1 to about nucleotide 614 of SEQ ID NO:1. The 3' fragment contained nucleotide 518 to about nucleotide 3220 of SEQ ID NO:1. The entire gene was then reconstructed by cloning both halves together into the pCRScript vector using an unique BamH1 restriction site. The full length gene was completely sequenced (SEQ ID NO:1). The first in frame methionine was preliminary assigned as the first amino acid in the protein, although there is no direct evidence for translation starting at this point. An AAUAA polyadenylation signal was found 1.3kb downstream of the stop codon (nucleotide 3172 of SEQ ID NO:1) for the longest predicted open reading frame. Using this assignment, the calculated molecular weight of the hStau protein was 55 kD, which agrees with the size of the protein identified on western blots (FIG. 2).

Production of Antibodies

Antibodies for L22 were generated using a synthetic peptide that corresponds with the N terminal region of the protein (CMAPVKKLVVKGG, SEQ ID NO:7). The peptide was coupled to KLH using standard procedures and antisera were raised in rabbits. To generate antibodies to hStau, the partial cDNA that was obtained in the initial three hybrid library was subcloned into the bacterial expression vector pGEX. This construct generated an N terminal fusion of GST with the C-terminal 448 amino acids of hStau (pLS 144A, i.e., residues 49 to 496 of SEQ ID NO:2). The fusion protein was overexpressed in bacteria, purified over a glutathione column using standard procedure (Pharmacia Biotech), and used to generate antibodies in rabbits (Covance Research Products Inc.)

Antisera from rabbits were initially screened for protein or peptide binding using an ELISA assay. Positive antisera then were tested for specificity on western blots and by immunoprecipitation. The antisera against L22 recognized a 15kD protein as expected in both cell lysates and in immunoprecipitations. Antibodies directed against hStau recognized an approximately 55kD protein in western blots on extracts and immunoprecipitations. This molecular weight is similar to the calculated molecular weight for the full length gene.

Northern and Western Analysis

Multi-tissue northern blots (Clontech) were hybridized with a 0.7 kb BamHI-EcoRI hStau cDNA probe according to the manufacturer's procedures. In particular, blots were hybridized at 68° C. in ExpressHyb solution (Clontech) for 1 hour with shaking. Blots were washed several times in 2×SSC, 0.05% SDS at room temperature, with a final wash in 0.1×SSC and 0.1% SDS at 60° C. for about 40 minutes. The blots then were re-probed with an actin probe without stripping the hStau signal. Signal intensity was quantified on a BAS 1500 PhosphorImager system (Fuji Medical System, Inc, Stamford, Conn.). Western analysis and immunoprecipitations (IP) were carried out according to Harlow, E. and D. Lane, *Antibodies: A Laboratory Manual*, Cold Spring Harbor Laboratory Press, Cold Spring Harbor, N.Y., 1988. Human 293 cells were lysed using either NP40 (up to 1%) buffer or hypotonic buffer and used for western and IP analysis. Some hStau IP were done using hStau serum that was coupled to CNBr activated sepharose beads to avoid IgG bands having a similar molecular weight as hStau in the western analysis.

Reverse-transcriptase-PCR

RT-PCR was used to quantitate RNAs in the supernatant and pellet of IP reactions. RNAs were prepared from both supernatant and pellet fractions by phenol/chloroform extraction and ethanol precipitation. The same amount of total RNA was then used in first strand cDNA synthesis reactions using random hexamer primers and Superscript II reverse transcriptase (BRL). cDNAs then were PCR amplified using hTR, U2, U3, 7SL, or RNase P specific primers. The primers used are as follows: hTR, 5'-GCCTGGGAGGGGTGGTGGCCATTTTTTG-3' (SEQ ID NO:3) and 5'-GTTTGCTCTAGAATGAACGGTGGAAG-3' (SEQ ID NO:4); U2, 5'-ATCGCTTCTCGGCCTTTT-3' (SEQ ID NO:8) and 5'-GGGTGCACCGTTCCTGGGA-3' (SEQ ID NO:9); U3, 5'-GACTATACTTTCAGGGATCATTTC-3' (SEQ ID NO:10) and 5'-CCACTCAGACCGCGTTCTCTC-3' (SEQ ID NO:11); 7SL, 5'-GTGCCTGTAGTCCCAGCTAC-3' (SEQ ID NO:12) and 5'-GAGACGGGGTCTCGCTATG-3' (SEQ ID NO:13); RNase P, 5'-GGAAGGTCTGAGACTAG-3' (SEQ ID NO:14) and 5'-ATCTCCTGCCCAGTCTG-3'(SEQ ID NO:15). Number of PCR cycles was adjusted for each amplification such that PCR amplification was in the linear range. Typically, 25 cycles were used to amplify hTR, whereas 18 cycles were used to amplify U2 and RNase P RNAs. For U3 and 7SL RNAs, 18 to 22 cycles generally were used. To control for genomic DNA contamination, cDNA synthesis reactions also were done in the absence of the reverse transcriptase. No signals were generated in the subsequent PCR reactions. PCR products were separated in 6% native polyacrylamide gel, dried and exposed. Signal intensities were quantified on a STORM PhosphorImager system (Molecular Dynamics, Inc, Sunnyvale, Calif.).

hStau Copy Number Estimate

To estimate hStau protein copy number in 293 cells, serial dilutions of 293 total cell lysate and a recombinant fusion protein GST-hStauC (described above) were western blotted and probed with either crude antisera or affinity purified hStau antibody. The signal intensity from 293 extract was compared to that obtained from known amounts of recombinant protein and copy number was estimated accordingly. For example, intensity of the hStau band (55 kD) from 20 µg total protein from 293 extract was equivalent to that obtained on 10–20 ng of GST-hStauC (83 kD) recombinant proteins.

Telomerase assay

Cell extracts, immunoprecipitation supernatants, or pellet fractions were assayed in a two step telomerase assay (TRAP) similar to that previously described by Autexier, C. et al., *EMBO J.*, 1996, 15(21):5928–5935. This two step procedure uses a limited number of PCR cycles for amplification of the telomerase products so that the signal will be in the linear range. Thus, relative signal intensities reflect relative activity in a semi quantitative manner. Negative controls were used that had either no extract or were RNase treated. An internal standard for product amplification in the PCR step of the assay also was included in each reaction.

Example 2

Identification of Telomerase-associated Proteins

To identify proteins that bind to the human telomerase RNA (hTR), a modified three-hybrid system was used. A region of the human telomerase RNA (nucleotide 64 to 222), which can form a potential stem loop structure, was fused to the MS2 phage RNA and expressed in yeast behind the RNaseP RNA polymerase III promoter. This region of hTR is required for activity in an in vitro reconstitution assay. Three different human cDNA-GAD fusion libraries were screened for proteins that interact with hTR. Several candidate were identified and the partial cDNAs clones were tagged with the HA epitope. These tagged clones were used to transfect 293 cells to test whether they would interact with hTR in human cells. Two proteins were identified which showed specific association with hTR after immunoprecipitation with HA antibody. The first protein was ribosomal associated protein L22, which also binds EBER (EBV encoded RNA) in EBV infected cells. The second protein was called telomerase-associated protein 3 (TEP3) or hStau (see below).

The full length cDNA encoding hStau was obtain from testis cDNA using a RACE technique. The hStau cDNA encodes a 496 amino acid open reading frame with a 1.3 kb long 3' untranslated region. A motif search revealed several regions of the protein that contain homology to double stranded RNA binding domains that were originally identified in the Drosophila Staufen protein. The conserved double stranded RNA binding domains include both full length and short domains and are present in a diverse group of proteins including *E. coli* RNase III, Xenopus rbpa, human double stranded RNA activated kinase (DAI, also called protein kinase RNA binding protein or pKR), and the human TAR binding protein that binds HIV RNA. The hStau protein identified herein, like other double stranded RNA binding domain proteins, has two full length and two short domains. The organization of the domains in hStau is similar to that of Drosophila Staufen although hStau is shorter (FIG. 1A). Furthermore, hStau sequence is most homologous to the Staufen protein, although this similarity is limited to the RNA binding domains (FIG. 1B). This suggests hStau uses Staufen related motifs to bind to RNA.

Example 3

Interaction With hTR in vivo

Figure 2A:
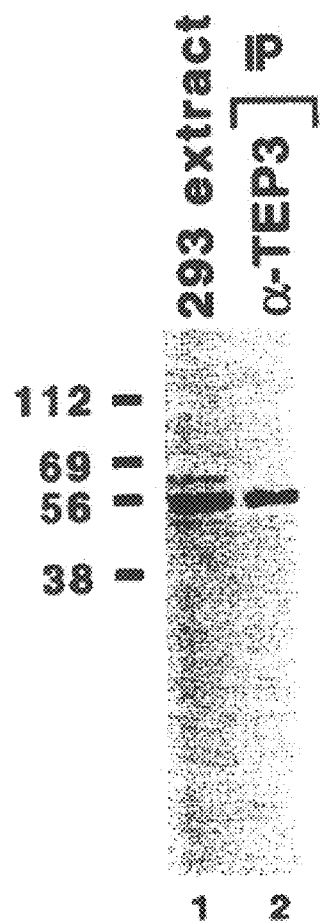
FIGS. 2A and 2B are Western blots that indicate hStau antibody (2A) and L22 antibody (2B) specificity.
Figure 2B:
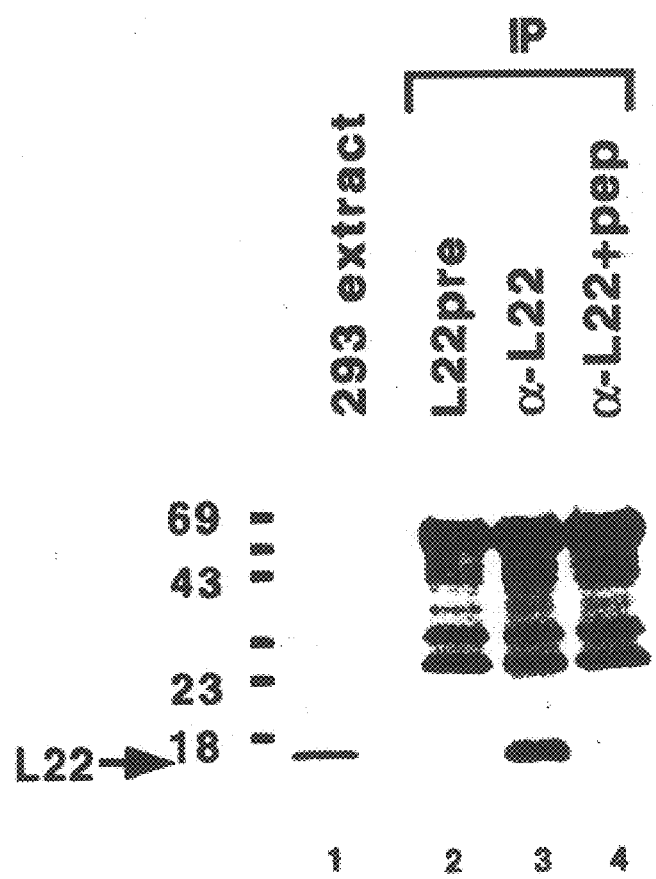

To further examine the interaction of L22 and hStau with hTR in vivo, antibodies to both proteins were generated and used to test the ability of the antibodies to precipitate hTR. For L22, anti-peptide antibodies were made, while for hStau, antibodies to a recombinant GST fusion protein were generated as described in Example 1. Immunoprecipitation and western blotting showed that these antibodies were specific for the appropriate proteins (FIGS. 2A and B). The L22 antibody precipitated a 15 kD protein that was not seen using pre-immune serum or when the peptide was pre-incubated with the antibody before the IP (FIG. 2B). Anti-hStau antibody recognized a 55 kD protein on western blots of both cell lysates and immunoprecipitation reactions, consistent with its calculated molecular weight. (FIG. 2A).

Figure 2C:
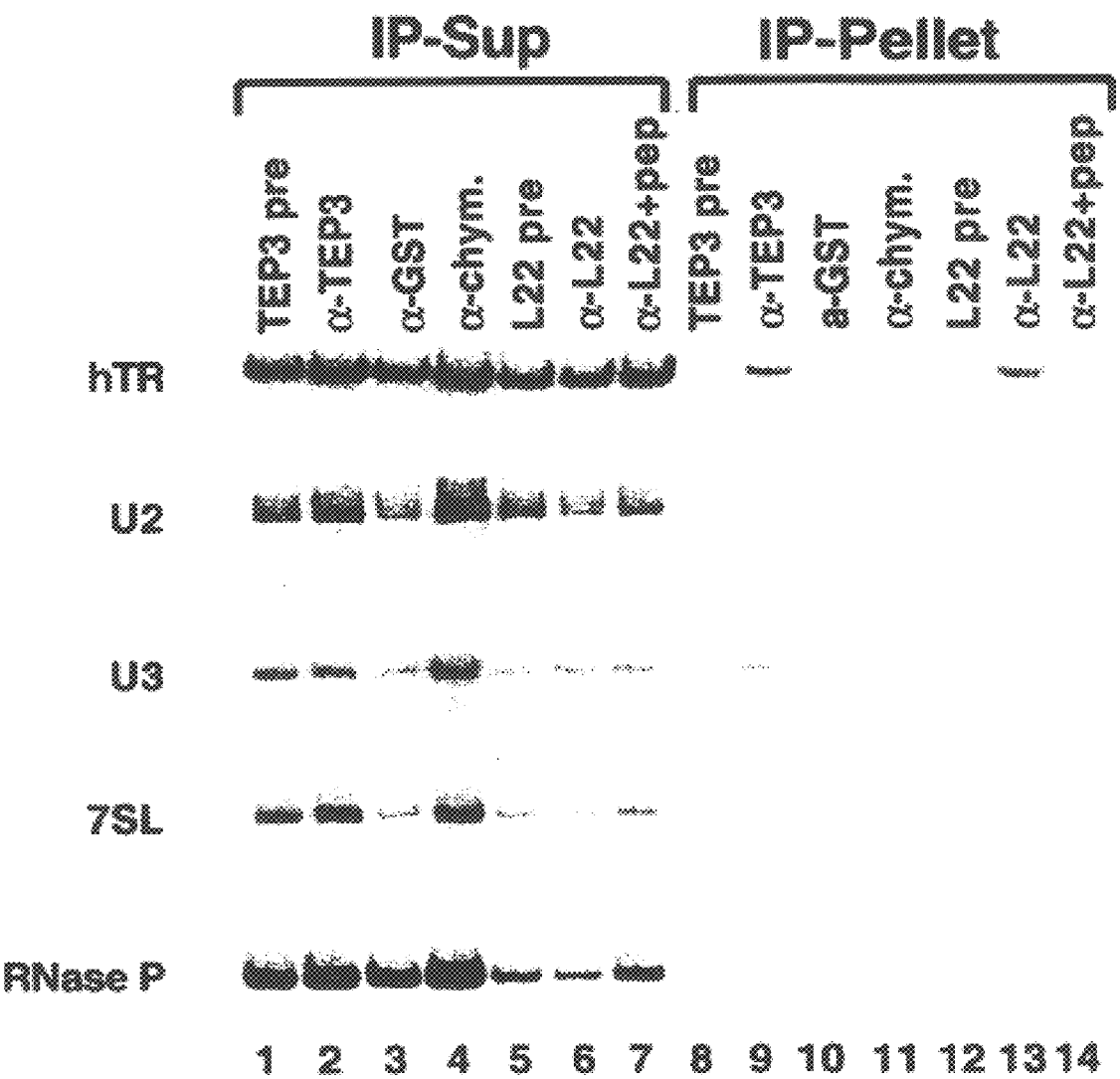
FIG. 2C is an RT-PCR analysis of RNAs in the supernatant (lane 1–7) and pellet (lane 8–14) fractions of hStau and L22 immunoprecipitation reactions. Lanes 1 and 8, hStau precipitation using pre-immune serum; lanes 2 and 9, precipitation using anti-hStau antibody; lanes 3 and 10, precipitation using anti-GST antibody; lanes 4 and 11, precipitation using anti-chymotrypsin antibody; lanes 5 and 12, precipitation using L22 pre-immune serum; lanes 6 and 13; precipitation using anti-L22 antibody; lanes 7 and 14, precipitation using anti-L22 antibody pre-incubated with L22 peptide. The RNAs amplified in the fractions are indicated on the left (hTR, U2, U3, 7SL, and RNase P).
Figure 2D:
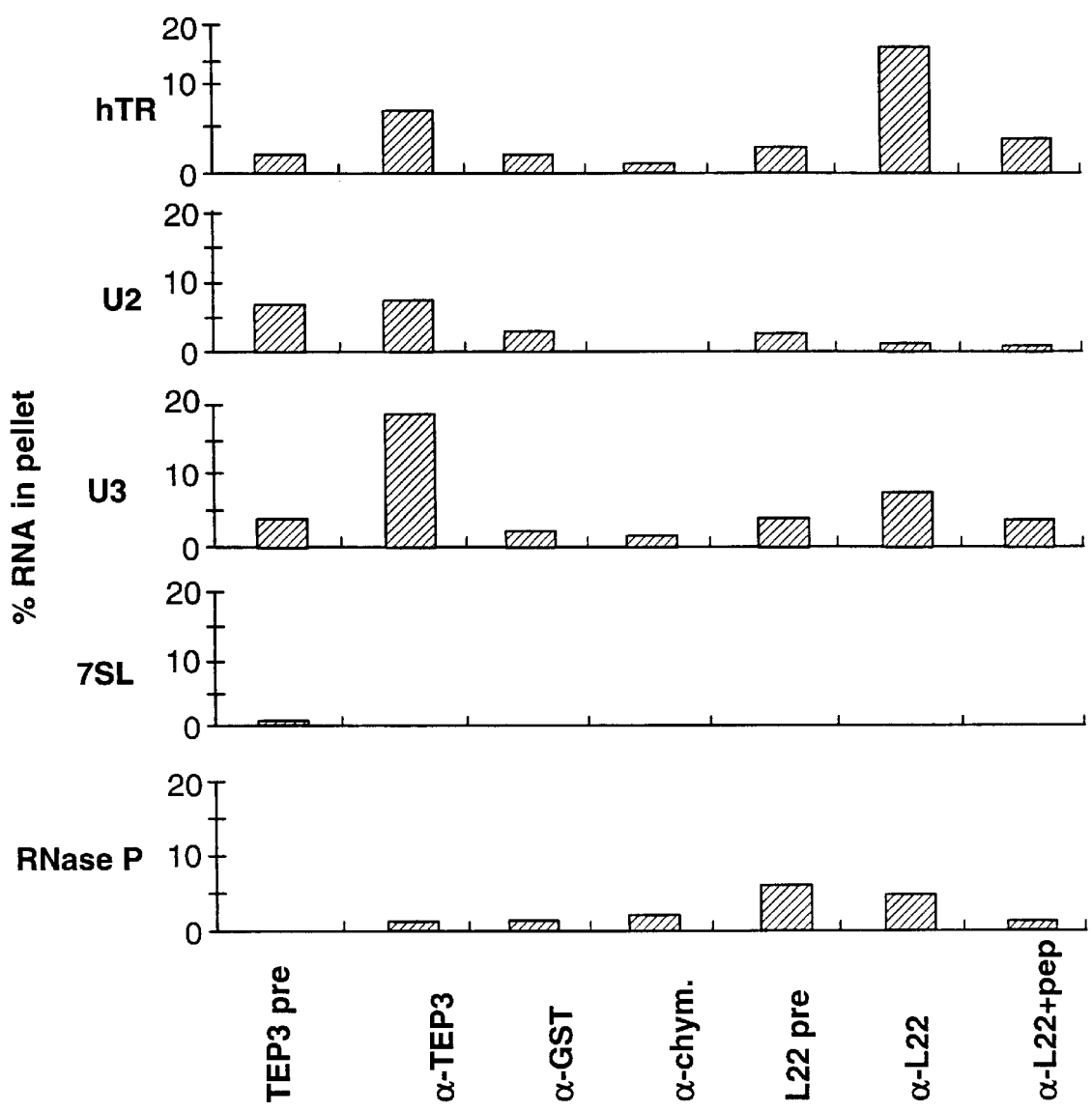
FIG. 2D is a quantitation of RNAs precipitated in FIG. 2C. The percentage of the RNA in the pellet is expressed as a fraction of the total signal intensity obtained in both pellet and supernatant. RNAs assayed are indicated on the left and antibodies used are indicated on the bottom.

To examine whether L22 and hStau interact with hTR in vivo, immunoprecipitations were carried out on 293 cell lysates using antibodies against L22 and hStau, as well as several unrelated antibodies as controls. The amount of hTR was measured in the supernatant and pellet fraction of the immunoprecipitation reactions (FIG. 2C). hTR was present in the pellets of the anti-hStau and anti-L22 reactions, but not in the pellets from the pre-immune sera or when anti-L22 antibody was pre-incubated with L22 peptides. To test for the specificity of the association, two unrelated antibodies, anti-GST and anti-chymotrypsin, were used. Telomerase RNA was not found in the pellet fraction of immunoprecipitation reactions with these antibodies. As a second control for specificity of the interaction with hTR, it was determined if four unrelated abundant small RNAs (U2, U3, 7SL RNA, and RNase P RNA) also were precipitated by the L22 and hStau antibodies (FIGS. 2C and D). Most of these RNAs were not detected at significant levels in the immunoprecipitation pellets, although some U3 was detected in the pellet fraction of anti-hStau precipitation, it was not clear how specific this interaction was. The precipitation of U3 could be due to the high copy number of this RNA ($2\times10_5$ per cell) compared to the hTR, which is only present at 500 copies per cell. These data suggest that hStau and L22 specifically associate with hTR in vivo.

Example 4 hStau and L22 Interact With Telomerase

Figure 3A:
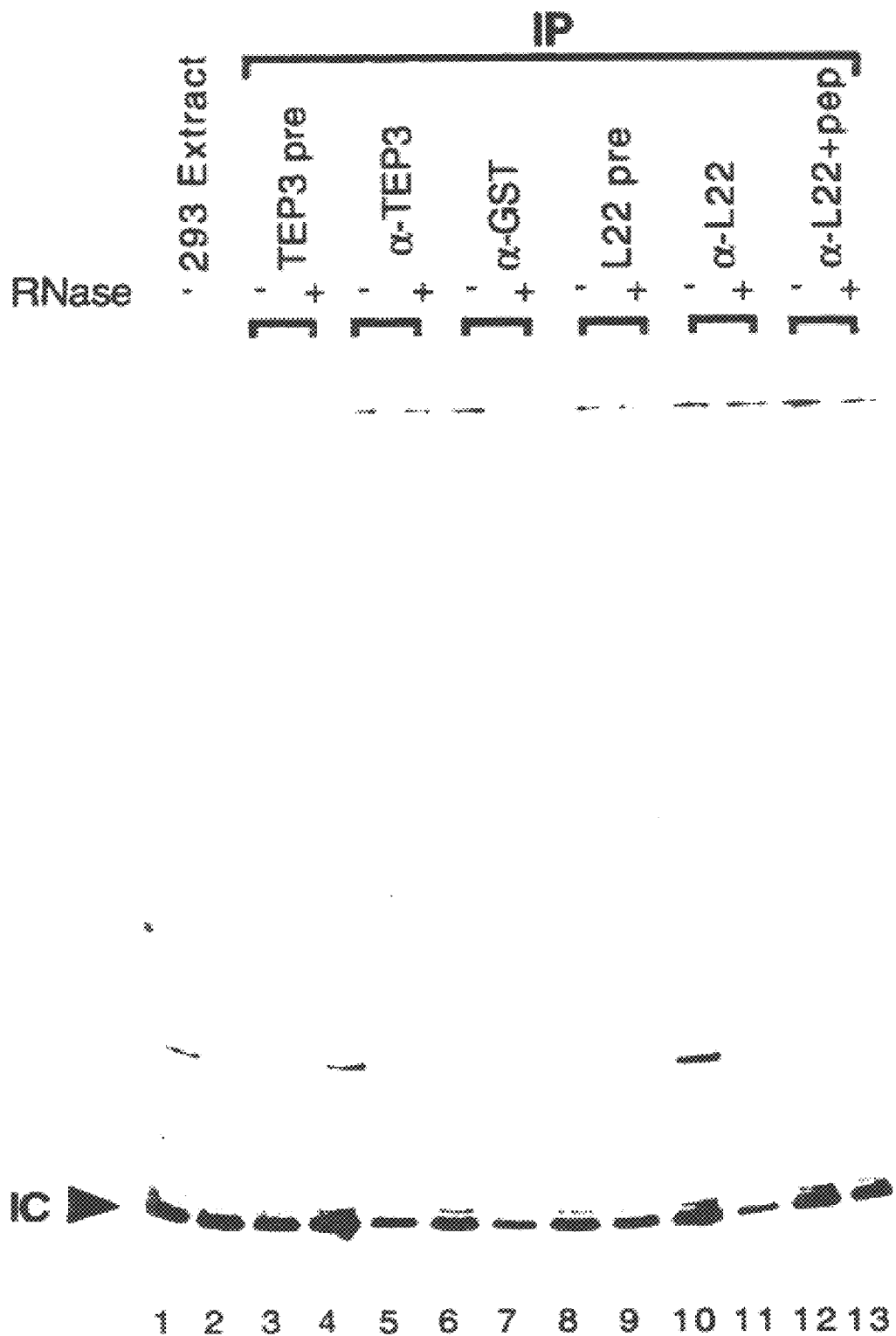
FIGS. 3A and 3B are autoradiographs that indicate hStau and L22 interact with telomerase (3A) and hTERT (3B).

To determine if hStau or L22 were associated with telomerase activity in vivo, telomerase activity was assayed in anti-hStau and anti-L22 immunoprecipitates. Immunoprecipitations were carried out using either anti-hStau, anti-L22, pre-immune serum, or an unrelated anti-GST antibody. Pellet fractions were washed with telomerase reaction buffer and a TRAP assay was performed. Telomerase activity was specifically immunoprecipitated with anti hStau antisera. Little activity was seen in immunoprecipitations with pre-immune sera and none with the anti-GST antibody (FIG. 3a). Activity also was precipitated with anti-L22 antisera. Pre-incubation of the anti-L22 antisera with the L22 peptide significantly reduced the level of telomerase activity precipitated. Thus, both hStau and L22 are associated with telomerase activity in vivo.

Figure 3B:
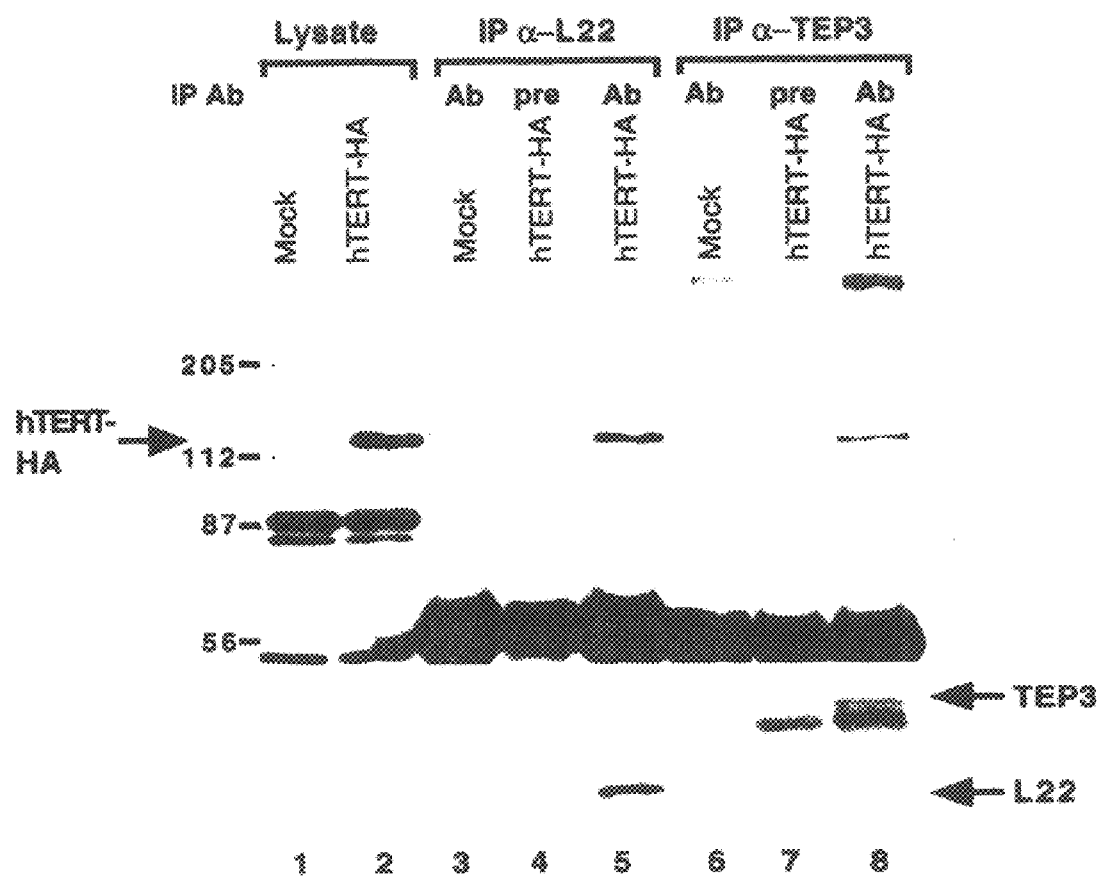

Telomerase activity requires the catalytic subunit hTERT. To look directly at the association of hStau and L22 with hTERT, 293 cells were transfected with a cDNA that expresses hTERT tagged with the HA epitope. Cell extracts were made and antibodies directed against hStau and L22 were used in immunoprecipitation reactions. Western analysis of the pellet fraction was carried out using anti-HA antibodies. hTERT was precipitated by both anti-hStau and anti-L22 antisera, but not by pre-immune sera (FIG. 3b). These results indicate that hStau and L22 protein associate with hTERT in vivo.

Example 5

Expression of hStau in Human Tissues

Figure 4A:
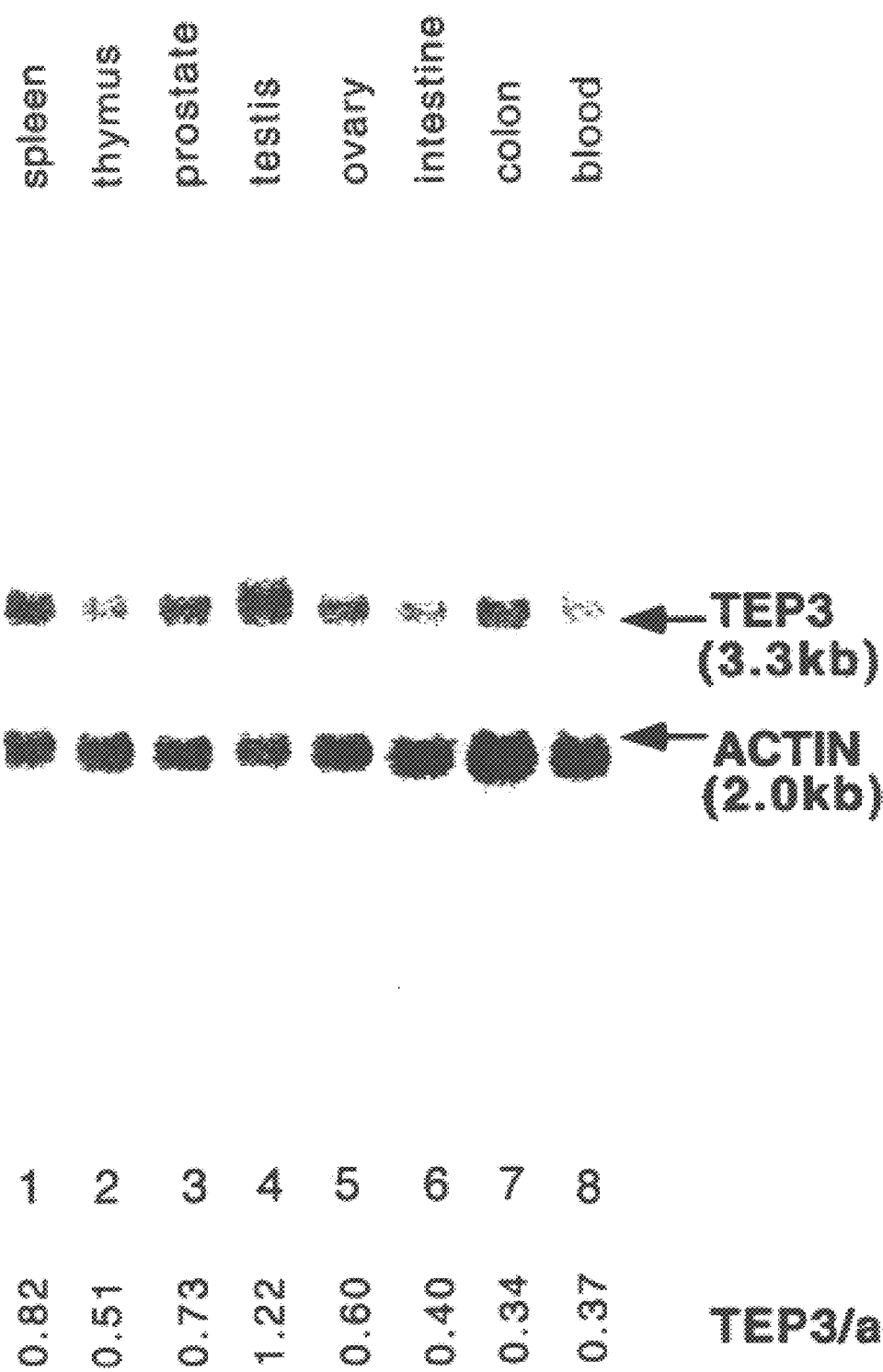
FIGS. 4A and 4B are Northern blots that indicate hStau mRNA expression in human tissues. Tissues from which RNAs were extracted are indicated at the top of the gel. The arrows indicate the sizes of the hStau (3.3 kb) and β-actin message (2.0 kb). For each gel, the amount of hStau relative to β-actin was quantified and the ratio is given for each lane at the bottom of the gel. Two filters were hybridized separately in different experiments, thus the values for hStau/actin ratio of the two gels can not be compared directly to each other.
Figure 4B:
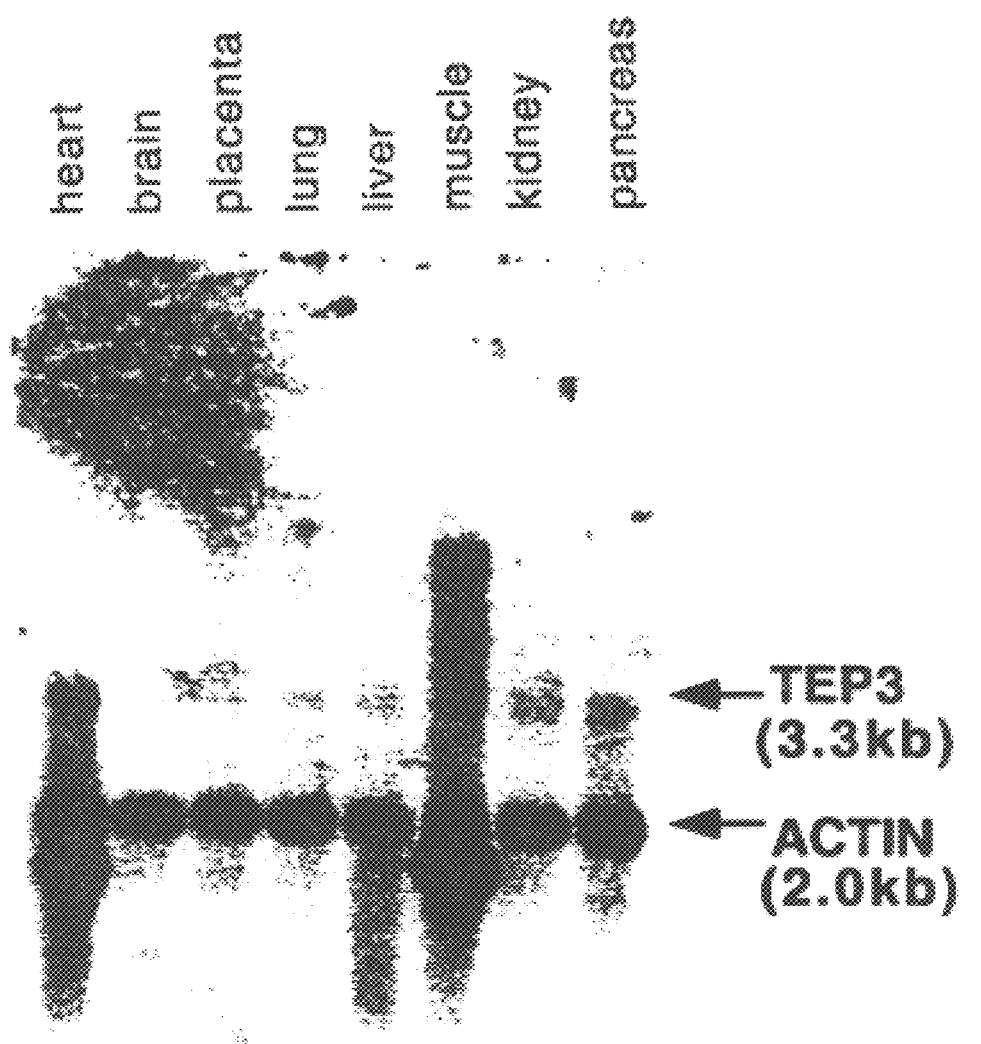

It has been demonstrated that L22 is widely expressed in cell lines. See, Toczyski, D. P. and J. A. Steitz, *Mol. Cell. Biol.,* 1993, 13:703–710. Determination of the expression pattern of L22 was carried out by northern analysis. Under conditions of high stringency, the L22 probe identified three different transcripts in most human tissues suggesting there are either multiple spliced forms or multiple genes that encode this protein. Human Staufen expression was determined by both northern and western analyses. Northern analysis identified a 3.3 kb RNA that hybridized at high stringency to the hStau probe. This size was expected from the size of the cDNA clone. This RNA was expressed at similar levels in a wide variety of human tissues (FIGS. 4A and 4B), with a slightly higher level in testes. Thus, hStau is widely expressed in a variety of tissues.

L22 protein has been estimated to be present at approximately 107 copies per cell. To determine the level of hStau in cells, a dilution series of known amounts of recombinant GST-hStau fusion protein was compared with a dilution series of 293 cell extracts. From this data, it was estimated that there were approximate 106 copies of hStau per cell in the human 293 cell line.

The presence of a long untranslated 3' region on the hStau cDNA suggested that it might be subject to translational regulation. To test whether the pattern of protein expression matched that of the RNA, western analysis was carried out on cell lysate from a variety of human tissues. The hStau protein was detected in protein lysates made from lung, kidney, testis and ovary, but not in brain and heart. Interestingly, the level was highest in the ovary and testes, which express telomerase in vivo. The discrepancy between the level of hStau protein in various tissues with the level of the RNA, suggests that hStau may be regulated by post transcriptional controls.

Example 6

Interactions Among Telomerase-associated Proteins

Figure 5A:
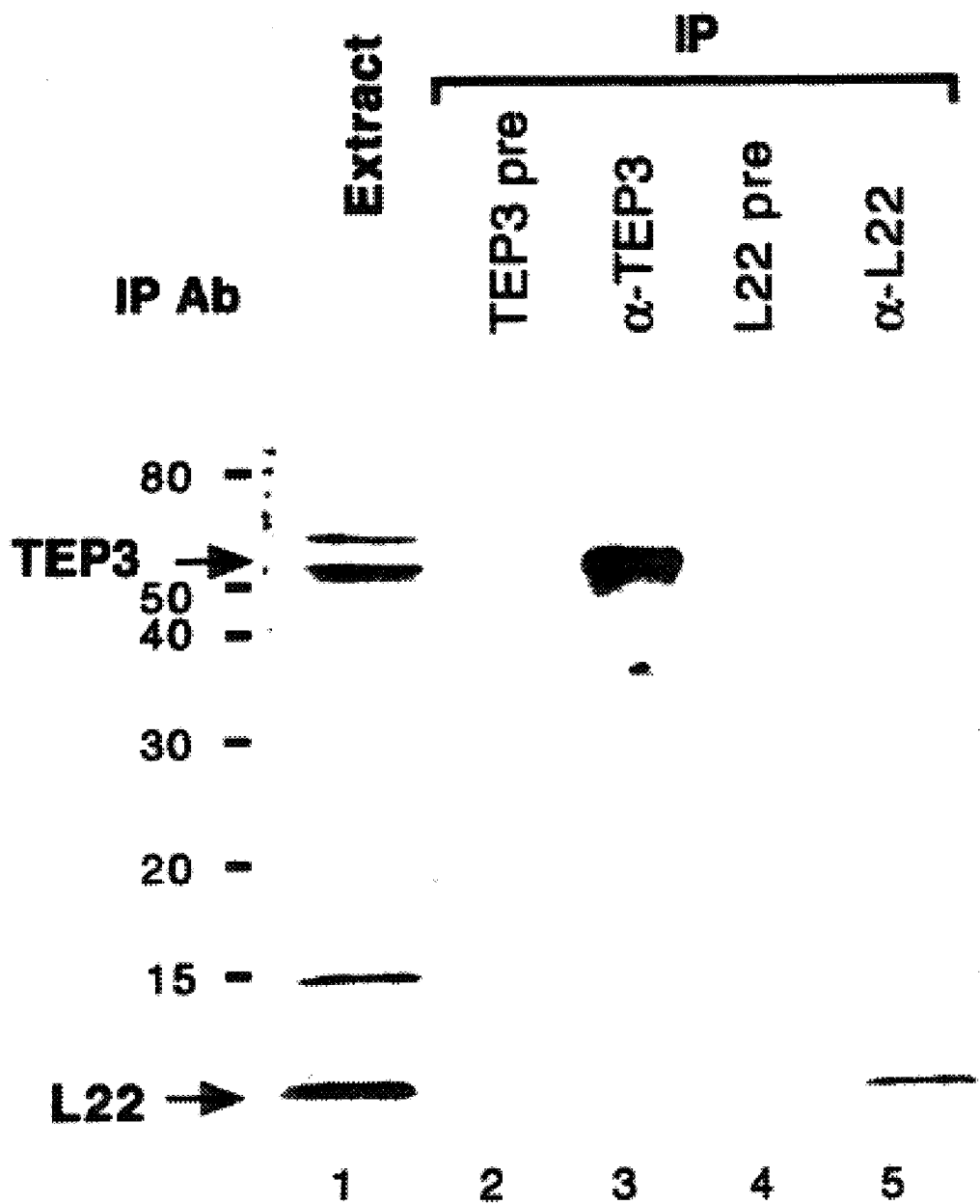
FIGS. 5A–5C are Western blots that examine interactions between telomerase-associated proteins.

To test whether hStau or L22 interact with each other or with telomerase-associated protein 1 (TEP1), immunoprecipitation reactions were carried out. TEP1 is a homologue of the Tetrahymena p80 telomerase component, and interacts with hTERT in vivo. Harrington, L. et al., *Science,* 1997, 275:973–977. Antibodies directed against hStau immunoprecipitated hStau but not L22. Similarly, antibodies directed against L22 brought down L22 but not hStau (FIG. 5A). These results suggested that hStau and L22 do not interact with each other. TEP1 was not detected in the immunoprecipitation reactions with either hStau or L22. The lack of a signal may have been, however, due to low affinity of the TEP1 antibody. For example, immunoprecipitation using TEP1 antibody brought down only very low levels of TEP1 and no hStau was detected.

Figure 5B:
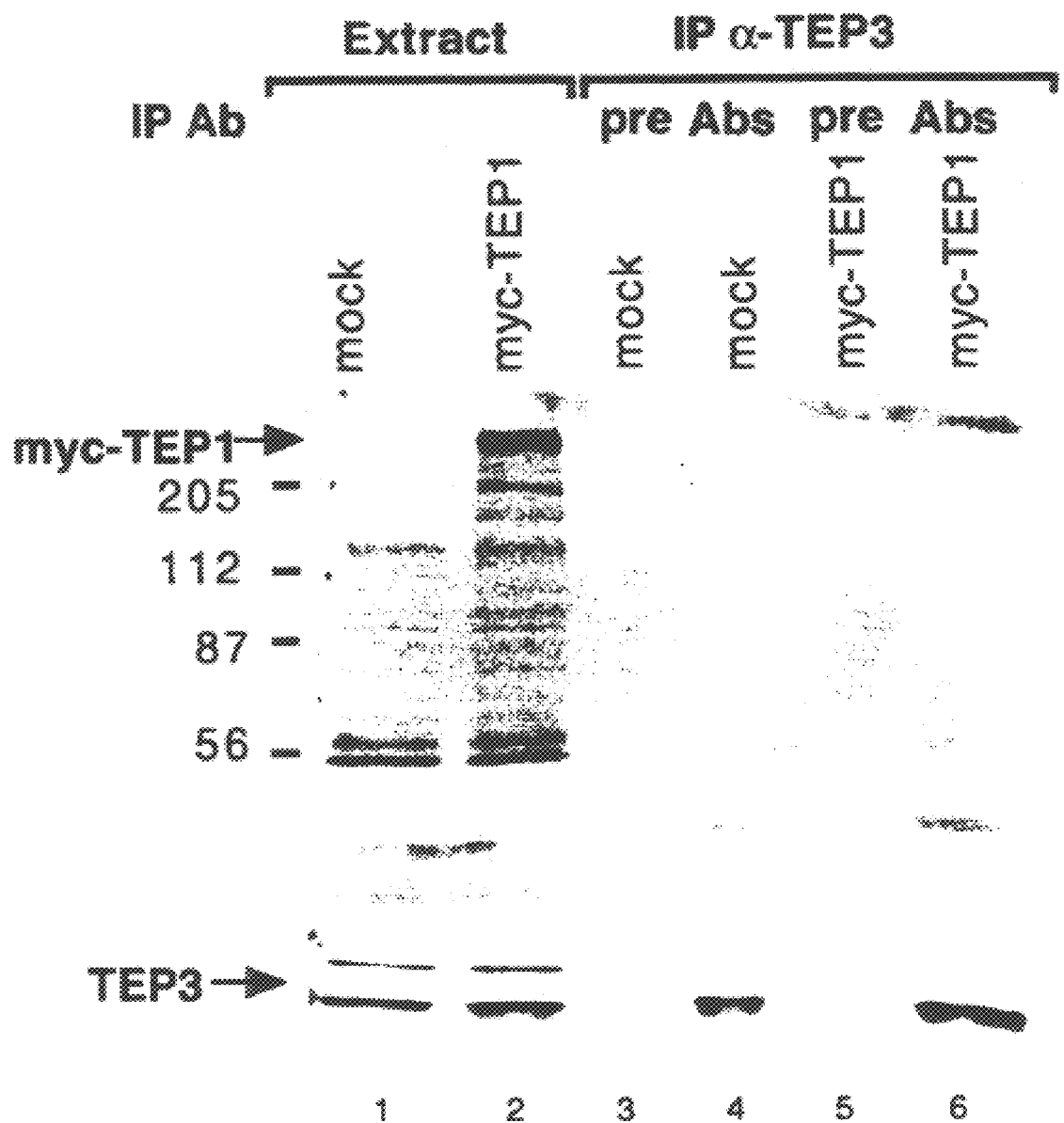
Figure 5C:
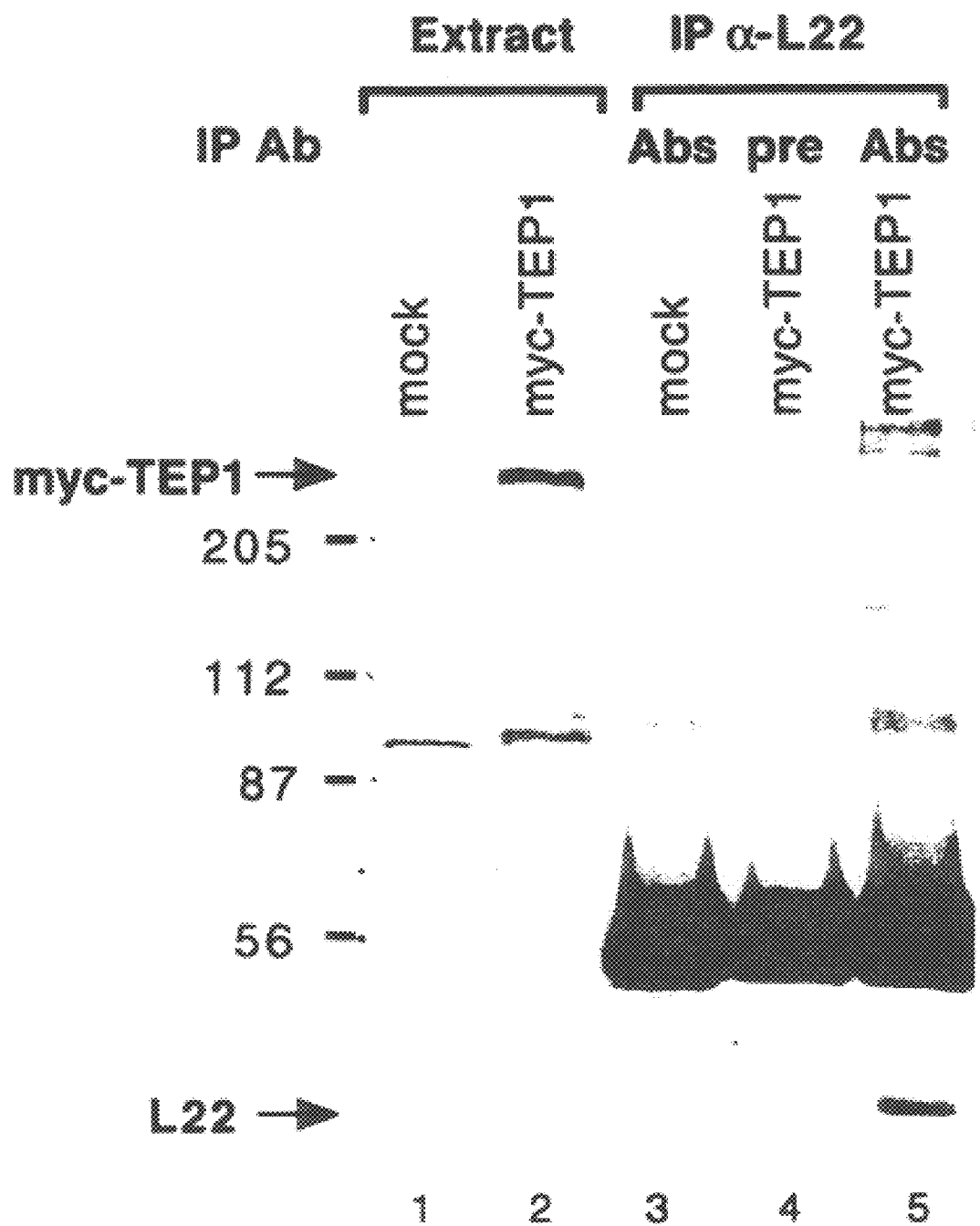

To further examine the interaction of hStau and L22 with TEP1, 293 cells transfected with expression plasmids for myc-tagged TEP1 were used. In cells expressing myc-tagged TEP1, anti-hStau antibody immunoprecipitated hStau, but TEP1 was not detected by western analysis probing for the myc tag (FIG. 5B). Similarly, anti-L22 antibody immunoprecipitated L22, but not myc-tagged TEP1 from myc-TEP1 expressed cells. (FIG. 5C). However, myc-TEP1 protein did co-immunoprecipitate with overexpressed hTERT-HA, indicating that this tagged TEP1 protein is associated with telomerase. Thus, these results suggest that TEP1, hStau and L22 are not associated with each other, yet they are individually associated with hTERT.

The inability to detect interactions between TEP1 and either hStau or L22 might be due to the low abundance of the complexes that contain both proteins, or it may indicate that these proteins are present in multiple distinct complexes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated polypeptide, wherein the polypeptide comprises the amino acid sequence of about residue 49 to about 496 of SEQ ID NO;2 or conservative subsitutions thereof.

2. The polypeptide of claim 1, wherein the polypeptide comprises the amino acid sequence of SEQ ID NO:2 or conservative substitutions thereof.

3. The polypeptide of claim 2, wherein the polypeptide comprises the amino acid sequence of SEQ ID NO:2.

4. The polypeptide of claim 1, wherein the polypeptide comprises the amino acid sequence of about residue 49 to about residue 496 of SEQ ID NO:2.

5. The polypeptide of claim 1, wherein the polypeptide binds RNA.

6. The polypeptide of claim 5, wherein the polypeptide binds double-stranded RNA.

7. The polypeptide of claim 5, wherein the polypeptide binds human telomerase RNA.

8. The polypeptide of claim 3, wherein the polypeptide has a molecular weight of about 55 kDa.

9. An isolated complex, wherein the complex comprises a polypeptide complexed with the catalytic subunit of telomerase, wherein the polypeptide comprises the amino acid sequence of about residue 49 to about residue 496 SEQ ID NO:2 or conservative substitutions thereof.

10. An isolated polynucleotide encoding a human staufen polypeptide, wherein the encoded polypeptide comprises the amino acid sequence of about residue 49 to about residue 496 of SEQ ID NO:2 or conservative substitutions thereof.

11. The polynucleotide of claim 10, wherein the encoded polypeptide comprises the amino acid sequence of about residue 49 to about residue 496 of SEQ ID NO:2 of conservative substitutions thereof.

12. The polynucleodide of claim 10, wherein the encoded polypeptide comprises the amino acid sequence of SEQ ID NO:2 or conservative substitutions thereof.

13. The polynucleotide of claim 10, wherein the polynucleotide has a nucleotide sequence at least 70% identical to the nucleotide sequence of nucleotides 345 to 1835 of SEQ ID NO:1.

14. The polynucleotide of claim 10, wherein the polynucleotide has a nucleotide sequence at least 80% identical to the nucleotide sequence of nucleotides 345 to 1835 of SEQ ID NO:1.

15. The polynucleotide of claim 10, wherein the polynucleotide has a nucleotide sequence at least 90% identical to the nucleotide sequence of nucleotides 345 to 1835 of SEQ ID NO:1.

16. The polynucleotide of claim 10, wherein the polynucleotide has a nucleotide sequence at least 95% identical to the nucleotide sequence of nucleotides 345 to 1835 of SEQ ID NO:1.

17. The polynucleotide of claim 10, wherein the polynucleotide comprises the nucleotide sequence of SEQ ID NO:1.

18. An expression vector comprising the polynucleotide of claim 10 operably linked to a regulatory sequence.

19. A cultured cell transfected with the vector of claim 18, wherein said cell expresses said polypeptide.

20. A method of producing a polypeptide, comprising culturing said cell of claim 19 under conditions permitting expression of said polypeptide.

21. A purified antibody having specific binding affinity for a human staufen polypeptide.

22. The antibody of claim 21, wherein the polypeptide comprises the amino acid sequence of SEQ ID NO:2.

23. The antibody of claim 21, wherein the antibody is polyclonal.

24. The antibody of claim 21, wherein the antibody is monoclonal.

* * * * *

UNITED STATES PATENT AND TRADEMARK OFFICE
CERTIFICATE OF CORRECTION

PATENT NO.     : 6,300,131 B1                                             Page 1 of 1
DATED          : October 9, 2001
INVENTOR(S)    : Siyuan Le and Carol W. Greider It is certified that error appears in the above-identified patent and that said Letters Patent is hereby corrected as shown below:

<u>Title page,</u>
Item [56], References Cited, after "Adams et al., "3400 new expressed sequence tags identify diversity of transcripts in human brain," *Nature Genetics,* 4:256-267" please insert -- (1993) --.

<u>Column 31,</u>
Line 27, before "496" please insert -- residue --.
Line 27, please delete "SEQ ID NO;2" and insert -- SEQ ID NO:2 -- therefor.
Line 47, between "496" and "SEQ" please insert -- of --.
Line 55, please delete "of" and insert -- or -- therefor.

Signed and Sealed this

Seventh Day of May, 2002

*Attest:*

*Attesting Officer*

JAMES E. ROGAN
*Director of the United States Patent and Trademark Office*